US012751954B2

(12) United States Patent
Smith et al.

(10) Patent No.: US 12,751,954 B2
(45) Date of Patent: Oct. 6, 2026

(54) METHODS FOR TREATING DRUG AND VACCINE INDUCED IMMUNE THROMBOCYTOPENIA BY ADMINISTERING SPECIFIC COMPOUNDS

(71) Applicant: Principia Biopharma Inc., Bridgewater, NJ (US)

(72) Inventors: Christopher W. Smith, Coventry (GB); Steve P. Watson, Droitwich (GB); Phillip L.R. Nicolson, Birmingham (GB); Claire Langrish, Redwood City, CA (US)

(73) Assignee: Principia Biopharma, Inc., Morristown, NJ (US)

( * ) Notice: Subject to any disclaimer, the term of this patent is extended or adjusted under 35 U.S.C. 154(b) by 396 days.

(21) Appl. No.: 18/555,388

(22) PCT Filed: Apr. 14, 2022

(86) PCT No.: PCT/US2022/024806
§ 371 (c)(1),
(2) Date: Oct. 13, 2023

(87) PCT Pub. No.: WO2022/221527
PCT Pub. Date: Oct. 20, 2022

(65) Prior Publication Data

US 2024/0207277 A1 Jun. 27, 2024

Related U.S. Application Data

(60) Provisional application No. 63/175,976, filed on Apr. 16, 2021.

(51) Int. Cl.
*A61K 31/519* (2006.01)
*A61P 7/02* (2006.01)
*A61P 7/04* (2006.01)

(52) U.S. Cl.
CPC .............. *A61K 31/519* (2013.01); *A61P 7/02* (2018.01); *A61P 7/04* (2018.01)

(58) Field of Classification Search
CPC ............. A61K 31/519; A61P 7/02; A61P 7/04
See application file for complete search history.

(56) References Cited

U.S. PATENT DOCUMENTS

| | | | |
|---|---|---|---|
| 4,721,710 | A | 1/1988 | Bernhart et al. |
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 5,514,711 | A | 5/1996 | Kitano et al. |
| 5,792,771 | A | 8/1998 | App et al. |
| 6,331,555 | B1 | 12/2001 | Hirth et al. |
| 6,391,452 | B1 | 5/2002 | Antonsen et al. |
| 6,410,486 | B2 | 6/2002 | Wetterich et al. |
| 6,596,746 | B1 | 7/2003 | Das et al. |
| 6,660,744 | B1 | 12/2003 | Hirst et al. |
| 7,217,682 | B2 | 5/2007 | Mori |
| 7,514,444 | B2 | 4/2009 | Honigberg et al. |
| 7,700,648 | B2 | 4/2010 | Mori |
| 8,673,925 | B1 | 3/2014 | Goldstein |
| 8,759,358 | B1 | 6/2014 | Goldstein |
| 8,828,426 | B2 | 9/2014 | Shah et al. |
| 8,940,744 | B2 | 1/2015 | Owens et al. |
| 8,946,241 | B2 | 2/2015 | Goldstein |
| 8,957,080 | B2 | 2/2015 | Goldstein et al. |
| 8,962,635 | B2 | 2/2015 | Goldstein |
| 8,962,831 | B2 | 2/2015 | Goldstein |
| 9,090,621 | B2 | 7/2015 | Goldstein |
| 9,266,895 | B2 | 2/2016 | Owens et al. |
| 9,376,438 | B2 | 6/2016 | Goldstein et al. |
| 9,572,811 | B2 | 2/2017 | Babler et al. |
| 9,688,676 | B2 | 6/2017 | Owens |
| 9,994,576 | B2 | 6/2018 | Owens et al. |
| 10,092,569 | B2 | 10/2018 | Masjedizadeh et al. |
| 10,456,403 | B2 | 10/2019 | Masjedizadeh et al. |
| 10,485,797 | B2 | 11/2019 | Gourlay |
| 10,533,013 | B2 | 1/2020 | Owens et al. |
| 10,828,307 | B2 | 11/2020 | Masjedizadeh et al. |
| 10,946,008 | B2 | 3/2021 | Gourlay |
| 11,040,980 | B2 | 6/2021 | Owens et al. |
| 11,369,613 | B2 | 6/2022 | Masjedizadeh et al. |
| 11,708,370 | B2 | 7/2023 | Phiasivongsa et al. |

(Continued)

FOREIGN PATENT DOCUMENTS

| | | | |
|---|---|---|---|
| AU | 2017290354 | B2 | 1/2019 |
| AU | 2020363873 | A1 | 4/2022 |

(Continued)

OTHER PUBLICATIONS

Storim, J., et al., "Dose-finding Phase 2 study to evaluate the efficacy and safety of the novel BTK inhibitor LOU064 in patients with CSU inadequately controlled by H1-antihistamines," Poster from 28th European Academy of Dermatology and Venereology Congress, Oct. 9-13, 2019 in Madrid, Spain.
Streicher, E., et al., "Distribution of thiocyanate between plasma and cerebrospinal fluid," American Journal of Physiology, vol. 206, No. 2, pp. 251-254 (1964).
Structure-Based Search Results (May 10, 2011, 10:04 AM), SciFinder.
Structure-Based Search Results (May 10, 2011, 10:20 AM), SciFinder.
Structure-Based Search Results (May 10, 2011, 10:46 AM), SciFinder.
Structure-Based Search Results (May 9, 2011, 8:13 PM), SciFinder.
Structure-Based Search Results (May 9, 2011, 8:23 PM), SciFinder.
Structure-Based Search Results (May 9, 2011, 8:33 PM), SciFinder.
Structure-Based Search Results (May 9, 2011, 9:06 PM), SciFinder.

(Continued)

*Primary Examiner* — Timothy R Rozof
(74) *Attorney, Agent, or Firm* — McNeill PLLC

(57) ABSTRACT

Methods for treating and/or preventing drug-induced thrombocytopenia (DITP) and vaccine-induced thrombosis and thrombocytopenia syndrome (VITT) with certain BTK inhibitors and/or pharmaceutically acceptable salts thereof are provided.

19 Claims, 4 Drawing Sheets

(56) References Cited

U.S. PATENT DOCUMENTS

| | | | |
|---|---|---|---|
| 11,814,390 B2 | 11/2023 | Phiasivongsa et al. | |
| 11,872,229 B2 | 1/2024 | Ferdous et al. | |
| 12,178,818 B2 | 12/2024 | Gourlay et al. | |
| 12,336,999 B2 | 6/2025 | Ferdous et al. | |
| 12,410,176 B2 | 9/2025 | Phiasivongsa et al. | |
| 2003/0153752 A1 | 8/2003 | Hirst et al. | |
| 2003/0187001 A1 | 10/2003 | Calderwood et al. | |
| 2004/0006083 A1 | 1/2004 | Hirst et al. | |
| 2004/0157847 A1 | 8/2004 | Field et al. | |
| 2005/0008640 A1 | 1/2005 | Waegell et al. | |
| 2005/0026945 A1 | 2/2005 | Kafka et al. | |
| 2005/0065176 A1 | 3/2005 | Field et al. | |
| 2006/0025383 A1 | 2/2006 | Wishart et al. | |
| 2006/0058297 A1 | 3/2006 | Roifman et al. | |
| 2006/0058324 A1 | 3/2006 | Capraro et al. | |
| 2006/0079494 A1 | 4/2006 | Santi et al. | |
| 2006/0275376 A1 | 12/2006 | Guimberteau et al. | |
| 2007/0149464 A1 | 6/2007 | Billen et al. | |
| 2007/0149550 A1 | 6/2007 | Billen et al. | |
| 2007/0197510 A1 | 8/2007 | Ohmoto et al. | |
| 2007/0232668 A1 | 10/2007 | Priebe et al. | |
| 2007/0232688 A1 | 10/2007 | Orchansky et al. | |
| 2008/0076921 A1 | 3/2008 | Honigberg et al. | |
| 2008/0146643 A1 | 6/2008 | Billen et al. | |
| 2008/0176865 A1 | 7/2008 | Billen et al. | |
| 2008/0260818 A1 | 10/2008 | Penhasi et al. | |
| 2009/0215750 A1 | 8/2009 | Bamberg et al. | |
| 2009/0215788 A1 | 8/2009 | Elworthy et al. | |
| 2009/0306396 A1 | 12/2009 | Toyoshima et al. | |
| 2010/0113520 A1 | 5/2010 | Miller | |
| 2010/0144705 A1 | 6/2010 | Miller | |
| 2010/0152143 A1 | 6/2010 | Priebe et al. | |
| 2010/0254905 A1 | 10/2010 | Honigberg et al. | |
| 2010/0280035 A1 | 11/2010 | Becker et al. | |
| 2011/0021518 A1 | 1/2011 | Magnuson et al. | |
| 2011/0086866 A1 | 4/2011 | Chen et al. | |
| 2012/0028981 A1 | 2/2012 | Miller | |
| 2012/0071497 A1 | 3/2012 | Buggy et al. | |
| 2012/0149687 A1 | 6/2012 | Lee et al. | |
| 2013/0079327 A1 | 3/2013 | Yamamoto et al. | |
| 2013/0116245 A1 | 5/2013 | Crawford et al. | |
| 2013/0197014 A1 | 8/2013 | Chen et al. | |
| 2013/0344116 A1 | 12/2013 | Wong et al. | |
| 2014/0094459 A1 | 4/2014 | Goldstein et al. | |
| 2014/0142099 A1 | 5/2014 | Owens | |
| 2014/0221398 A1 | 8/2014 | Goldstein et al. | |
| 2014/0256734 A1 | 9/2014 | Lawson et al. | |
| 2014/0303161 A1 | 10/2014 | Goldstein et al. | |
| 2014/0303190 A1 | 10/2014 | Goldstein | |
| 2014/0364410 A1 | 12/2014 | Owens et al. | |
| 2015/0094295 A1 | 4/2015 | Owens et al. | |
| 2015/0140085 A1 | 5/2015 | Goldstein | |
| 2015/0209432 A1 | 7/2015 | Konda et al. | |
| 2015/0328310 A1 | 11/2015 | Allen et al. | |
| 2015/0353557 A1 | 12/2015 | Goldstein et al. | |
| 2015/0353562 A1 | 12/2015 | Goldstein | |
| 2016/0045503 A1 | 2/2016 | Goldstein et al. | |
| 2016/0113913 A1 | 4/2016 | Murakawa et al. | |
| 2016/0251358 A1 | 9/2016 | Owens et al. | |
| 2016/0257686 A1 | 9/2016 | Owens | |
| 2016/0376277 A1 | 12/2016 | Desai et al. | |
| 2017/0065591 A1 | 3/2017 | Masjedizadeh et al. | |
| 2018/0015088 A1 | 1/2018 | Nunn et al. | |
| 2018/0050027 A1* | 2/2018 | Gourlay | A61K 31/519 |
| 2018/0162861 A1 | 6/2018 | Goldstein et al. | |
| 2018/0193274 A1 | 7/2018 | Nunn et al. | |
| 2018/0305350 A1 | 10/2018 | Goldstein et al. | |
| 2018/0327413 A1 | 11/2018 | Owens et al. | |
| 2019/0076435 A1 | 3/2019 | Masjedizadeh et al. | |
| 2019/0231784 A1 | 8/2019 | Ferdous et al. | |
| 2019/0345159 A1 | 11/2019 | Goldstein et al. | |
| 2020/0038405 A1 | 2/2020 | Masjedizadeh et al. | |
| 2020/0101059 A1 | 4/2020 | Gourlay | |
| 2020/0190092 A1 | 6/2020 | Owens et al. | |
| 2021/0015821 A1 | 1/2021 | Masjedizadeh et al. | |
| 2021/0106583 A1 | 4/2021 | Neale et al. | |
| 2021/0106584 A1 | 4/2021 | Gourlay et al. | |
| 2021/0113567 A1 | 4/2021 | Ferdous et al. | |
| 2021/0113568 A1 | 4/2021 | Ariza | |
| 2021/0198264 A1 | 7/2021 | Phiasivongsa et al. | |
| 2021/0205312 A1 | 7/2021 | Nunn et al. | |
| 2021/0221818 A1 | 7/2021 | Phiasivongsa et al. | |
| 2022/0073522 A1 | 3/2022 | Owens et al. | |
| 2022/0370459 A1 | 11/2022 | Masjedizadeh et al. | |
| 2023/0124267 A1 | 4/2023 | Gourlay et al. | |
| 2023/0158031 A1 | 5/2023 | Langrish et al. | |
| 2023/0158033 A1 | 5/2023 | Neale et al. | |
| 2023/0399330 A1 | 12/2023 | By et al. | |
| 2024/0174676 A1 | 5/2024 | Owens et al. | |
| 2024/0182484 A1 | 6/2024 | Phiasivongsa et al. | |
| 2024/0207275 A1 | 6/2024 | Ferdous et al. | |
| 2024/0207277 A1 | 6/2024 | Smith et al. | |
| 2025/0084085 A1 | 3/2025 | Comte et al. | |
| 2025/0108054 A1 | 4/2025 | Daak et al. | |
| 2025/0221999 A1 | 7/2025 | Gourlay et al. | |
| 2025/0255874 A1 | 8/2025 | Daak et al. | |

FOREIGN PATENT DOCUMENTS

| | | | |
|---|---|---|---|
| CA | 2890111 | A1 | 5/2014 |
| CN | 1274280 | A | 11/2000 |
| CN | 1681483 | A | 10/2005 |
| CN | 1874761 | A | 12/2006 |
| CN | 101287452 | A | 10/2008 |
| CN | 101610676 | A | 12/2009 |
| CN | 101730699 | A | 6/2010 |
| CN | 101880243 | A | 11/2010 |
| CN | 102159214 | A | 8/2011 |
| CN | 101610676 | B | 3/2013 |
| CN | 103096716 | A | 5/2013 |
| CN | 101805341 | A | 7/2013 |
| CN | 101805341 | B | 7/2013 |
| CN | 103534258 | A | 1/2014 |
| CN | 104640861 | A | 5/2015 |
| CN | 104736178 | A | 6/2015 |
| CN | 104822681 | A | 8/2015 |
| CN | 103096716 | B | 3/2016 |
| CN | 105753863 | A | 7/2016 |
| CN | 103534258 | B | 9/2016 |
| CN | 106456652 | A | 2/2017 |
| CN | 107759602 | A | 3/2018 |
| CN | 109600989 | A | 4/2019 |
| CN | 110461315 | A | 11/2019 |
| CN | 110483521 | A | 11/2019 |
| CN | 106456652 | B | 9/2020 |
| CN | 115515687 | A | 12/2022 |
| EA | 027213 | B1 | 6/2017 |
| EA | 033900 | B1 | 12/2019 |
| EP | 0461546 | A2 | 12/1991 |
| EP | 0493767 | A2 | 7/1992 |
| EP | 0461546 | A3 | 3/1993 |
| EP | 0493767 | A3 | 3/1993 |
| EP | 0908457 | A1 | 4/1999 |
| EP | 2443929 | A1 | 4/2012 |
| EP | 2578585 | A1 | 4/2013 |
| EP | 2578585 | B1 | 7/2016 |
| EP | 3107544 | B1 | 12/2016 |
| FR | 2535721 | A1 | 5/1984 |
| GB | 2447933 | A | 10/2008 |
| JP | 5663950 | A | 5/1981 |
| JP | 021450 | A | 1/1990 |
| JP | 04177244 | A | 6/1992 |
| JP | 2005239657 | A | 9/2005 |
| JP | 2010504324 | A | 2/2010 |
| JP | 2010235628 | A | 10/2010 |
| JP | 2014513729 | A | 6/2014 |
| JP | 2014517838 | A | 7/2014 |
| JP | 2015522653 | A | 8/2015 |
| JP | 2015527401 | A | 9/2015 |
| JP | 2016503063 | A | 2/2016 |
| JP | 2017506243 | A | 3/2017 |
| JP | 6203848 | B2 | 9/2017 |
| JP | 2019519581 | A | 7/2019 |
| KR | 1020150053965 | A | 5/2015 |

(56) References Cited

FOREIGN PATENT DOCUMENTS

| | | | |
|---|---|---|---|
| KR | 1020160117614 | A | 10/2016 |
| KR | 102203990 | B1 | 1/2021 |
| RU | 2659777 | C2 | 7/2018 |
| WO | 9524190 | A2 | 9/1995 |
| WO | 9531432 | A1 | 11/1995 |
| WO | 9841499 | A1 | 9/1998 |
| WO | 9914216 | A1 | 3/1999 |
| WO | 9918938 | A1 | 4/1999 |
| WO | 0172751 | A1 | 10/2001 |
| WO | 02066463 | A1 | 8/2002 |
| WO | 03037890 | A2 | 5/2003 |
| WO | 03050080 | A1 | 6/2003 |
| WO | 03068157 | A2 | 8/2003 |
| WO | 03082807 | A2 | 10/2003 |
| WO | 2004014382 | A1 | 2/2004 |
| WO | 2004016259 | A1 | 2/2004 |
| WO | 2004074283 | A1 | 9/2004 |
| WO | 2005020929 | A2 | 3/2005 |
| WO | 2005023773 | A1 | 3/2005 |
| WO | 2005030184 | A2 | 4/2005 |
| WO | 2005085210 | A1 | 9/2005 |
| WO | 2006086634 | A2 | 8/2006 |
| WO | 2006134468 | A1 | 12/2006 |
| WO | 2007043401 | A1 | 4/2007 |
| WO | 2007087068 | A2 | 8/2007 |
| WO | 2007130075 | A1 | 11/2007 |
| WO | 2007142755 | A2 | 12/2007 |
| WO | 2008005954 | A2 | 1/2008 |
| WO | 2008006032 | A1 | 1/2008 |
| WO | 2007087068 | A3 | 2/2008 |
| WO | 2008039218 | A2 | 4/2008 |
| WO | 2008054827 | A2 | 5/2008 |
| WO | 2008061740 | A1 | 5/2008 |
| WO | 2008072053 | A2 | 6/2008 |
| WO | 2008072077 | A2 | 6/2008 |
| WO | 2008116064 | A2 | 9/2008 |
| WO | 2008121742 | A2 | 10/2008 |
| WO | 2009140128 | A2 | 11/2009 |
| WO | 2009143477 | A1 | 11/2009 |
| WO | 2010009342 | A2 | 1/2010 |
| WO | 2010014930 | A2 | 2/2010 |
| WO | 2010065898 | A2 | 6/2010 |
| WO | 2011031896 | A2 | 3/2011 |
| WO | 2011046964 | A2 | 4/2011 |
| WO | 2011060440 | A2 | 5/2011 |
| WO | 2011144585 | A1 | 11/2011 |
| WO | 2011152351 | A1 | 12/2011 |
| WO | 2011153514 | A2 | 12/2011 |
| WO | 2012021444 | A1 | 2/2012 |
| WO | 2012123502 | A1 | 9/2012 |
| WO | 2012158764 | A1 | 11/2012 |
| WO | 2012158795 | A1 | 11/2012 |
| WO | 2012158810 | A1 | 11/2012 |
| WO | 2012158843 | A2 | 11/2012 |
| WO | 2013003629 | A2 | 1/2013 |
| WO | 2013010136 | A2 | 1/2013 |
| WO | 2013010380 | A1 | 1/2013 |
| WO | 2013010868 | A1 | 1/2013 |
| WO | 2013010869 | A1 | 1/2013 |
| WO | 2013041605 | A1 | 3/2013 |
| WO | 2013059738 | A2 | 4/2013 |
| WO | 2013102059 | A1 | 7/2013 |
| WO | 2013116382 | A1 | 8/2013 |
| WO | 2013184572 | A1 | 12/2013 |
| WO | 2013185082 | A2 | 12/2013 |
| WO | 2013191965 | A1 | 12/2013 |
| WO | 2014004707 | A1 | 1/2014 |
| WO | 2014022569 | A1 | 2/2014 |
| WO | 2014039899 | A1 | 3/2014 |
| WO | 2014068527 | A1 | 5/2014 |
| WO | 2014078578 | A1 | 5/2014 |
| WO | 2014164558 | A1 | 10/2014 |
| WO | 2014171542 | A1 | 10/2014 |
| WO | 2015006504 | A1 | 1/2015 |
| WO | 2015095099 | A1 | 6/2015 |
| WO | 2015127310 | | 8/2015 |
| WO | 2015127310 | A1 | 8/2015 |
| WO | 2015132799 | A2 | 9/2015 |
| WO | 2015144857 | A1 | 10/2015 |
| WO | 2015149056 | A1 | 10/2015 |
| WO | 2016100914 | A1 | 6/2016 |
| WO | 2016105531 | A1 | 6/2016 |
| WO | 2016109221 | A1 | 7/2016 |
| WO | 2017041536 | A1 | 3/2017 |
| WO | 2017066014 | A1 | 4/2017 |
| WO | 2018005849 | A1 | 1/2018 |
| WO | 2018013918 | A2 | 1/2018 |
| WO | 2018136401 | A1 | 7/2018 |
| WO | 2019208805 | A1 | 10/2019 |
| WO | 2021072095 | A1 | 4/2021 |
| WO | 2021076514 | A1 | 4/2021 |
| WO | 2021127231 | A1 | 6/2021 |
| WO | 2021141919 | A1 | 7/2021 |
| WO | 2021150723 | A1 | 7/2021 |
| WO | 2021211782 | A1 | 10/2021 |
| WO | 2021216696 | A1 | 10/2021 |
| WO | 2022081512 | A1 | 4/2022 |
| WO | 2022221527 | A1 | 10/2022 |
| WO | 2023205153 | A1 | 10/2023 |
| WO | 2023232958 | A1 | 12/2023 |
| WO | 2023244562 | A1 | 12/2023 |
| WO | 2024097667 | A1 | 5/2024 |
| WO | 2024124113 | A1 | 6/2024 |
| WO | 2025006680 | A1 | 1/2025 |
| WO | 2025029842 | A2 | 2/2025 |
| WO | 2025090702 | A1 | 5/2025 |
| WO | 2025090703 | A1 | 5/2025 |
| WO | 2025122747 | A1 | 6/2025 |
| WO | 2025199134 | A1 | 9/2025 |
| WO | 2025217164 | A1 | 10/2025 |
| WO | 2026024765 | A1 | 1/2026 |
| WO | 2026024885 | A1 | 1/2026 |
| WO | 2026035812 | A1 | 2/2026 |

OTHER PUBLICATIONS

Tan, S., et al., "Targeting the SYK-BTK axis for the treatment of immunological and hematological disorders: Recent progress and therapeutic perspectives," Pharmacological Therapy, vol. 138, No. 2, pp. 294-309 (2013).

Taylor, I., et al., "Comparison of longevity and common tumor profiles between Sprague-Dawley and Han Wistar rats," Journal of Toxicology & Pathology, vol. 33, pp. 189-196 (2020).

Kamisawa, T., et al., "IgG4-related disease", The Lancet, vol. 385, No. 9976, pp. 1460-1471 (2015).

Unniappan, S., et al., "Leptin extends the anorectic effects of chronic PYY (3-36) administration in ad libitum-fed rats," American Journal of Physiology-Regulatory, Integrative and Comparitive Physiology, vol. 295, No. 1, pp. R51-R58 (2008).

Van Beek, N. et al., "Therapy of pemphigus", Hautarzt, Springer Verlag, Berlin, DE, vol. 70, No. 4, pp. 243-253 (Mar. 18, 2019).

Vayne, C., et al., "Pathophysiology and Diagnostic of Drug-Induced Immune Thrombocytopenia," Journal of Clinical Medicine, vol. 9, No. 7, p. 2212 (2020).

Verhe, R., et al., "Preparation of 2,2-Dialkylcyclopropanes Geminally Substituted with Electron-Withdrawing Groups," Synthesis, vol. 7, pp. 530-532 (1978).

Verhe, R., et al., "Synthesis of 1,1-BIS(HYDROXYMETHYL) Cyclopropanes," Organic Preparations and Procedures International, vol. 13, No. 1, pp. 13-18 (1981).

Verhe, R., et al., "Thermal Lactonization of Brominated Alkylidenemalonates: Synthesis of 2-Buten-4-Olides," Bulletin des Societes Chimiques Belges, vol. 87, No. 3, pp. 215-222 (1978).

Vo, N., et al., "Transformations of Resin-Bound Pyridinium Ylides: I. A Stereoselective Synthesis of 2,2,3-Trisubstituted Cyclopropanecarboxylates," Tetrahedron Letters, vol. 38, No. 46, pp. 7951-7954 (1997).

Von Hundelshausen, P., et al., "Vaccine-Induced Immune Thrombotic Thrombodytopenia (VITT): Targeting Pathomechanisms with

(56) References Cited

OTHER PUBLICATIONS

Bruton Tyrosine Kinase Inhibitors", Thrombosis and Haemostasis, vol. 121, No. 11, pp. 1395-1399 (2021).
Wang, G., et al., "Substituted 4-amino-1H-pyrazolo[3,4-d]pyrimidines as multi-targeted inhibitors of insulin-like growth factor-I receptor (IGFIR) and members of ErbB-family receptor kinases," Bioorganic Medicinal and Chemistry Letters, vol. 20, pp. 6067-6071 (2010).
Wang, K., et al., "Cyanoacetamide Multicomponent Reaction (I): Parallel Synthesis of Cyanoacetamides," Journal of Combinatorial Chemistry, vol. 11, pp. 920-927 (2009).
Weber, A., "Targeting the NLRP3 Inflammasome via BTK," Frontiers in Cell and Developmental Biology, vol. 9, p. 630479 (2021).
Weber, A., et al., "Bruton's tyrosine kinase: an emerging key player in innate immunity," Frontiers in Immunology, vol. 8, p. 1454 (2017).
Weber, K., "Differences in types and incidence of neoplasms in Wistar Han and Sprague-Dawley rats," Toxicology & Pathology, vol. 45, No. 1, pp. 64-75 (2017).
WebMD. 10 Ways to Prevent Psoriasis Flare-Ups. Web: (2016) .
WebMD. Multiple Sclerosis (MS)-Prevention. Web: < http://www.webmd.com/multiple-sclerosis/tc/multiple-sclerosis-ms-prevention> (2015).
Wells, G., et al., "Structural Studies on Bioactive Compounds. 32.1 Oxidation of Tyrphostin Protein Tyrosine Kinase Inhibitors with Hypervalent lodine Reagents," Journal of Medicinal Chemistry, vol. 43. pp. 1550-1562 (2000).
WhatisDryEye.com. Dry Eye vs. Conjunctivitis Web: (2016).
Wilding, I., et al., "Targeting of Drugs and Vaccines to the Gut," Pharmacology and Therapeutics, vol. 62, pp. 97-124 (1994).
Wissner, A., et al., "Synthesis and Structure-Activity Relationships of 6,7-Disubstituted 4-Anilinoquinoline-3-carbonitriles. The Design of an Orally Active, IrreversibleInhibitor of the Tyrosine Kinase Activity of the Epidermal Growth Factor Receptor (EGFR) and the Human Epidermal Growth Factor Receptor-2 (HER-2)," Journal of Medicinal Chemistry, vol. 46, pp. 49-63 (2003).
Wree, A., et al., "NLRP3 inflammasome activation results in hepatocyte pyroptosis, liver inflammation, and fibrosis in mice," Hepatology, vol. 59, No. 3, pp. 898-910 (2014).
Xu, D., et al., "RN486, a selective Bruton's tyrosine kinase inhibitor, abrogates immune hypersensitivity responses and arthritis in rodents," Journal of Pharmacology & Experimental Therapy, vol. 341, pp. 90-103 (2012).
Yamaguchi, T., "Mutagenicity of Isothiocyanates, Isocyanates and Thioureas on Salmonella typhimurium," Agricultural Biology & Chemistry, vol. 44, No. 12, pp. 3017-3018 (1980).
Zanella, A., et al., "Treatment of autoimmune hemolytic anemias," Haematologica, vol. 99, No. 10, pp. 1547-1554 (2014).
Zhang, D., et al., "Recent Advances in BTK Inhibitors for the Treatment of Inflammatory and Autoimmune Diseases," Molecules, vol. 26, No. 16, p. 4907 (2021).
Zhang, F., et al., "Organic base catalyzed carbonyl allylation of methyl trifluoropyruvate with activated alkenes," Tetrahedron Letters, vol. 65, pp. 83-86 (2009).
Zimmerman, H., et al., "The Diverted Di-π-Methane Rearrangement; Mechanistic and Exploratory Organic Photochemistry," Organic Letters, vol. 4, No. 7, pp. 1155-1158 (2002).
Bobkova, I., et al., "Modern view on the treatment of membranous nephropathy," Therapeutic archive, vol. 6, pp. 99-104 (2020).
Kholodov, et al., "Clinical Pharmacokinetics," Medicine, pp. 83-98, 134-138, 160, 378-380 (1985). English translation also provided.
Principia Biopharma: "A Study of PRN1008 in Adult Patients with Pemphigus Vulgaris", ClinicalTrials.gov, (Mar. 10, 2016).
Wong, J.D., "The ruthless player in purpura: immune thrombocytopenia purpura," https://tpech.gov.taipei/mp109181/News_Content.aspx?n=80359412498D4193&sms =D6D8C221F7AECFEE&s=0419C614DFB65D7A, Sep. 4, 2012.
Qi, Sheng et al., Physical stabilization of low-molecular-weight amorphous drugs in the solid state: a material science approach, Ther. Deliv. (2014), 5(7): 817-841 (25 pages).
Rodeghiero, Francesco, "Recent progress in ITP treatment", International Journal of Hematology, 117:316-330 (2023).
Schutt et al., "Inhibition of BTK and ITK with Ibrutinib Is Effective in the Prevention of Chronic Graft-versus-Host Disease in Mice", PLOS ONE, vol. 10, No. 9, p. e0137641, (2015).
Smith et al., "Antiplatelet drugs block platelet activation by VITT patient serum," Blood 138 (25): pp. 2733-2740, (2021).
Smith et al., "Selective Btk inhibition by PRN1008/PRN473 blocks human CLEC-2, and PRN473 reduces venous thrombosis formation," Blood Adv. 8(21), pp. 5557-5570 (2024).
Tan et al., "Identification of LRRK2 Inhibitors through Computational Drug Repurposing", ACS Chem Neurosci., Feb. 1, 2023;14(3), pp. 481-493.
Vogel, S. et al., "NLRP3 Inflammasome-Mediated Platelet Activation and Thrombus Formation in Sickle Cell Mice Can be Targeted By the BTK Inhibitor Ibrutinib", Blood, vol. 142, No. Supplement 1, pp. 3935-3936 (2023).
Vogel, S. et al., "NLRP3 inflammasome and bruton tyrosine kinase inhibition interferes with upregulated platelet aggregation and in vitro thrombus formation in sickle cell mice", Biochemical and Biophysical Research Communications, Elsevier, Amsterdam NL, vol. 555, pp. 196-201 (2021).
Vogel, S. et al., "The NLRP3 Inflammasome in Platelets Is Upregulated in Sickle Cell Disease and Promotes Platelet Aggregation and in Vitro Thrombosis", Blood, Amsterdam, NL, vol. 130, p. 2234, abstract (2017).
Vogel, S. et al., "The platelet NLRP3 inflammasome is upregulated in sickle cell disease via HMGB1/TLR4 and Bruton tyrosine kinase", Blood Advances, vol. 2, No. 20, pp. 2672-2680 (2018).
Vranic, Edina, "Amorphous Pharmaceutical Solids," Bosnian Journal of Basic Medical Sciences, 4(3): pp. 35-39 (2004).
Wedi, Bettina, "Emerging treatments for chronic urticaria", Expert Opinion on Investigational Drugs, 31:3, pp. 281-290, (2022) DOI: 10.1080/13543784.2022.2042513.
Xiao et al., "Development of New Drugs for Autoimmune Hemolytic Anemia", Pharmaceutics, vol. 14, No. 5, pp. 1-23 (2022).
Yu et al., "Amorphous pharmaceutical solids: preparation, characterization and stabilization," Advanced Drug Delivery Reviews 48; pp. 27-42 (2001).
Zeiser, Robert, et al., "Three US Food and Drug Administration-approved therapies for chronic GVHD", Blood, American Society of Hematology, US, vol. 139, No. 11, pp. 1642-1645, (2022).
Zeng et al., "State-of-the-art review of human autoimmune blistering diseases (AIBD)", Vet Dermatol, 32, p. 524-e145 (2021).
McKenzie, C., et al., "Cellular immune dysfunction in immune thrombocytopenia," British Journal of Haematology, vol. 163, pp. 10-23 (2013).
MedicineNet.com. Definition of Cancer. Web: (2004).
MedlinePlus. Autoimmune Diseases, Web: (2014).
Metz, M., et al., "Fenebrutinib in H1 antihistamine-refractory chronic spontaneous urticaria: a randomized phase 2 trial," Nature Medicine, vol. 27, No. 11, pp. 1961-1969 (2021).
Meydan, N., et al., "Inhibition of acute lymphoblastic leukaemia by a Jak-2 inhibitor," Nature, vol. 379, pp. 645-648 (1996).
Michel, M., "Classification and therepeutic approaches in autoimmune hemolytic anemia: an update," Expert Review of Hematology, vol. 4, No. 6, pp. 607-618 (2011).
Michel, M., et al., "A randomized and double-blind controlled trial evaluating the safety and efficacy of rituximab for warm autoimmune hemolytic anemia in adults (the RAIHA study)," American Journal of Hematology, vol. 92, No. 1, pp. 23-27 (2017).
Miller, R., "Electrophilic Fragment-Based Design of Reversible Covalent Kinase Inhibitors," Journal of the American Chemical Society, vol. 135, No. 14, pp. 5298-5301 (2013).
Mohamed, A., et al., Bruton's tyrosine kinase (Btk): function, regulation, and transformation with special emphasis on the PH domain, Immunology Review, vol. 228, pp. 58-73 (2009).
Montillo, M., et al., "Ibrutinib in previously treated chronic lymphocytic leukemia patients with autoimmune cytopenias in the RESONATE study," Blood Cancer Journal 7, No. e524 Letter to the Editor (2017).
Mosher, K., et al., "Go with your gut: microbiota meet microglia," Nature Neuroscience, vol. 18, pp. 930-931 (2015).

(56) References Cited

OTHER PUBLICATIONS

Murrell, D., et al., "A Pilot Study of the Efficacy of a Bruton's Tyrosine Kinase Inhibitor in the Treatment of Dogs with Pemphigus Foliaceus", Australasian Journal of Dermatology, vol. 58, No. S1, p. 73 (Jan. 1, 2017).
Murrell, D., et al., "Diagnosis and Management of Pemphigus: recommendations by an International Panel of Experts," Journal of American Academy of Dermatology, vol. 82, No. 3, pp. 575-585 (2020).
Nagasawa, H., et al., "Inhibitory effects of potassium thiocyanate on normal and neoplastic mammary development in female mice," European Journal of Cancer, vol. 16, No. 4, pp. 473-480 (1980).
Nakamura, M. et al., "Diquafosol Ophthalmic Solution for Dry Eye Treatment," Advances in Therapy, vol. 29, No. 7, pp. 579-589 (2012).
Newman, K., et al., "Management of immune cytopenias in patients with systemic lupus erythematosus," Autoimmunity Reviews, vol. 12, No. 7, pp. 784-791 (2013).
Neys, S., et al., "Targeting Bruton's Tyrosine Kinase in Inflammatory and Autoimmune Pathologies," Frontiers in Cell & Developmental Biology, vol. 9, p. 668131 (2021).
Outerbridge, C., et al., "A new treatment for autoimmune blistering diseases—the efficacy of the Bruton's tyrosine kinase inhibitor PRN473 in canine pemphigus foliaceus," Journal of American Academy of Dermatology, No. 3530, p. AB141 (2016).
Pan, Z. et al., "Discovery of Selective Irreversible Inhibitors for Bruton's Tyrosine Kinase," ChemMedChem, vol. 2, pp. 58-61 (2007).
Patani, G., et al., "Bioisosterism: A Rational Approach in Drug Design," Chemical Reviews, vol. 96, pp. 3147-3176 (1996).
Peng, T., et al., "Data on the drug release profiles and powder characteristics of the ethyl cellulose based microparticles prepared by the ultra-fine particle processing system," Data in Brief, vol. 29, p. No. 105629, pp. 1-6 (Feb. 8, 2020).
Pennington, L., et al., "The Necessary Nitrogen Atom: A Versatile High-Impact Design Element for Multiparameter Optimization," Journal of Medicinal Chemistry, vol. 60, No. 9, pp. 3552-3579 (2017).
Porro, A., et al., "Pemphigus vulgaris," Anais Brasileiros de Dermatologia, vol. 94, No. 3, pp. 264-278 (2019).
Porter, D., et al., "The discovery of potent, orally bioavailable pyrimidine-5-carbonitrile-6-alkyl CXCR2 receptor antagonists," Bioorganic and Medicinal Chemistry Letters, vol. 24, pp. 3285-3290 (2014).
Press Release, "Sanofi to acquire Principia Biopharma," Aug. 17, 2020.
Proenca, F., et al., "A simple and eco-friendly approach for the synthesis of 2-imino and 2-oxo-2H-chromene-3-carboxamides,"Green Chemistry, vol. 10, pp. 995-998 (2008).
Rankin, A., et al., "Selective inhibition of BTK prevents murine lupus and antibody-mediated glomerulonephritis," Journal of Immunology, vol. 191, No. 9, pp. 4540-4550 (2012).
Rellos, P., et al., "Structure and Regulation of the Human Nek2 Centrosomal Kinase," Journal of Biological Chemistry, vol. 282, No. 9, pp. 6833-6842 (2007).
Rip, J., et al., "The role of Bruton's tyrosine kinase in immune cell signaling and systemic autoimmunity," Critical Reviews in Immunology, vol. 38, No. 1, pp. 17-62 (2018).
Robak, T., et al., "Tyrosine kinase inhibitors as potential drugs for B-cell lymphoid malignancies and autoimmune disorders," Expert Opinion on Investigational Drugs, vol. 21, No. 7, pp. 921-947 (2012).
Rodeghiero, F., "A critical appraisal of the evidence for the role of splenectomy in adults and children with ITP," British Journal of Haematology, vol. 181, No. 2, pp. 183-195 (2018).
Rogers, K., et al., "Incidence and description of autoimmune cytopenias during treatment with ibrutinib for chronic lymphocytic leukemia," Leukemia, vol. 30, pp. 346-350 (2016).
Roumier, M., et al., "Characteristics and outcome of warm autoimmune hemolytic anemia in adults: New insights based on a single-center experience with 60 patients," American Journal of Hematology, vol. 89, No. 9, pp. E150-E155 (2014).
Sadeghi, F., et al., "The influence of drug type of the release profiles from Surelease-coated pellets," International Journal of Pharmaceuticals, vol. 254, pp. 123-135 (2003).
Saloojee, Y., et al., "Carboxyhaemoglobin and plasma thiocyanate: complementary indicators of smoking behaviour," Thorax, vol. 37, No. 7, pp. 521-525 (1982).
Sammes, M., et al., "α-Cyano-sulphonyl Chlorides: Their Preparation and Reactions with Amines, Alcohols, and Enamines," Journal of the Chemical Society, pp. 2151-2155 (1971).
Sanofi Press Release: Rilzabrutinib LUNA 3 phase 3 study met primary endpoint in immune thrombocytopenia, Apr. 23, 2024.
Santilli, A., et al., "8,9,10,11-Tetrahydro-12H-benzo[5,6]quinoxalino[2,3-e][1,4]diazepin-12-ones. Examples of a New Heterocyclic Ring System," Journal of Organic Chemistry, vol. 29, pp. 2066-2068 (1964).
Santus, G., et al., "Osmotic Drug Delivery: A Review of the Patent Literature," Journal of Controlled Release, vol. 35, pp. 1-21 (1995).
Schwab, I., et al., "Intravenous immunoglobulin therapy: how does IgG modulate the immune system?," Nature Reviews Immunology, vol. 13, pp. 176-189 (2013).
Schwarz, J., et al., "Novel Cyclopropyl β-Amino Acid Analogues of Pregabalin and Gabapentin That Target the α2-δ Protein," Journal of Medicinal Chemistry, vol. 48, pp. 3026-3035 (2005).
Schwobel, J., et al., "Prediction of Michael-Type Acceptor Reactivity toward Glutathione," Chemical Research in Toxicology, vol. 23, pp. 1576-1585 (2010).
Serafimova, I., et al., "Reversible targeting of noncatalytic cysteines with chemically tuned electrophiles," Nature Chemical Biology, vol. 8, No. 5, pp. 471-476 (2012).
Shekunov, B., et al., "Crystallization processes in pharmaceutical technology and drug delivery design", Journal of Crystal Growth, vol. 211, No. 104, Apr. 1, 2000, pp. 122-136.
Sideras, P., et al., "Molecular and cellular aspects of X-linked agammaglobulinemia," Advanced Immunology, vol. 59, pp. 135-223 (1995).
Smith, P., et al., "A phase I trial of PRN1008, a novel reversible covalent inhibitor of Bruton's tyrosine kinase, in healthy volunteers: A phase I study of PRN1008", British Journal of Clinical Pharmacology, vol. 83, No. 11, pp. 2367-2376 (Aug. 1, 2017).
Stahl, P., et al., (Eds.) Handbook of Pharmaceutical Salts: Properties, Selection, and Use, Wiley-VCH; pp. 1-374 (2002).
Stevens, C., et al., "Synthesis of Substituted Cyclopropylphosphonates by Michael Induced Ring Closure (MIRC) Reactions," Synlett, vol. 7, pp. 1089-1092 (2002).
Stone, J., et al., "Recommendations for the nomenclature of lgG4-related disease and its individual organ system manifestations", Arthritis & Rheumatism, vol. 64, No. 10, pp. 3016-3067 (2012).
U.S. Appl. No. 63/176,543, filed Apr. 19, 2021, Christopher W. Smith.
"Solubility, Polymorphism, Crystallinity, and Crystal Habit of Acetaminophen and Ibuprofen by Initial Solvent Screening," PharmaTech.com, Vol. 30, No. 10, pp. 1-3 (2006).
"Supplement Article", The Authors, British Journal of Haematology, vol. 185, suppl. 1, pp. 3-202 (2019).
2012 ICD-9-CM Diagnosis Code 372.30: Conjunctivitis, unspecified, retrieved Aug. 4, 2016 (1 page).
Abdulahad, W., et al., "Immune regulation and B-cell depletion therapy i1 patients with primary Sjogren's syndrome," J Autoimmun, 39(1): 103-111 (2012).
Abstract for Neplyuev, V., "Nitration and nitrosation of 1, 1,3,3-tetraacyl-1-propenes" Ukrainskii Khimicheskii Zhurnal (Russian Edition), 49(2):192-194 (1 page) (1983).
Abstract for Neplyuev, V., "Studies of triacylmethanes VII. 1, 1,3,3-Tetraacyl-3-arylazo-1-propenes," Zhurnal Organicheskoi Khimii, 15(3): 563-566 (1 page) (1979).
Advani, R., et al., "Bruton tyrosine kinase inhibitor ibrutinib (PCI-32765) has significant activity in patients with relapsed/refractory B-cell malignancies," Journal of Clinical Oncology, vol. 31, No. 1, pp. 88-94 (2013).
American Cancer Society. Can Non-Hodgkin's Lymphoma Be Prevented? Web: (2016).

(56) References Cited

OTHER PUBLICATIONS

American College of Rheumatology; ACR COVID-19 Vaccine Clinical Guidance Task Force, "COVID-19 vaccine clinical guidance summary for patients with rheumatic and musculoskeletal diseases," https://www.rheumatology.org/Portals/0/Files/COVID-19-Vaccine-Clinical-Guidance-Rheumatic-Diseases-Summary.pdf, cited May 10, 2021.
Anderson, R.C., et al., "Absorption and Toxicity of Sodium and Potassium Thiocyanates," Journal of American Pharmacists Association, vol. 29, No. 4, pp. 152-161 (1940).
Ansel, H., et al., "Pharmaceutical Dosage Forms and Drug Delivery Systems," Seventh Edition, Lippincott Williams & Wilkins, A Wolters Kluwer Company, Chapters 1-8, pp. 1-243 (1999).
Armesto, D., et al., "Efficient photochemical synthesis of 2-vinylcyclopropanecarbaldehydes, precursors of cyclopropane components present i1 pyrethroids, by using the oxa-di-TT-methane rearrangement," Tetrahedron, 66: 8690-8697 (2010).
Arnold, L., et al., "Pyrrolo[2,3-d]pyrimidines Containing an Extended 5-Substituent as Potent and Selective Inhibitors of Ick I," Bioorg. Med. Chem. Lett., 10:2167-2170 (2000).
Arora, A., et al., "Role of Tyrosine Kinase Inhibitors in Cancer Therapy," J Pharmacol. Exp. Ther., 315(3):971-979 (2005).
Audia, S., et al., "Pathogenesis of immune thrombocytopenia," Autoimmunity Reviews, vol. 16, pp. 620-632, Apr. 17, 2017.
Banerjee, K., et al., "Effect of thiocyanate ingestion through milk on thyroid hormone homeostasis in women," British Journal of Nutrition, vol. 78, No. 5, pp. 679-681 (1997).
Barcellini, W., et al., "Clinical heterogeneity and predictors of outcome in primary autoimmune hemolytic anemia: a GIMEMA study of 308 patients," Blood, vol. 124, No. 19, pp. 2930-2936 (2014).
Barker, M., "The Blood Cyanates in the Treatment of Hypertension," Journal of American Medical Association, vol. 106, No. 10, pp. 762-767 (1936).
Barker, M., et al., "Further Experiences with Thiocyanates," Journal of American Medical Association, vol. 117, No. 9, pp. 1591-1594 (1941).
Bartsch, R., et al., "Human relevance of follicular thyroid tumors in rodents caused by non-genotoxic substances," Regulatory Toxicology & Pharmacology, vol. 98, pp. 199-208 (2018).
Basheer, A., et al., "Enols of Substituted Cyanomalonamides," J Org. Chem. 72:5297-5312 (2007).
Bastin, R., et al., "Salt Selection and Optimisation Procedures for Pharmaceutical New Chemical Entities," Org.Process Res. Dev, 4:427-435 (2000).
Beissert, S., et al., "A comparison of oral methylprednisolone plus azathioprine or mycophenolate mofetil for the treatment of pemphigus," Archives of Dermatology, vol. 142, No. 11, pp. 1447-1454 (2006).
Berge, S., et al., "Pharmaceutical Salts," J Pharm. Sci., 66:1-19 (1977).
Bernhart, C., et al., "Synthesis and Antiarrhythmic activity of New [(Dialkylamino)alkyl]pyridylacetamides," J Med Chem., 26:451-455 (1983).
Bhandari, R.K., et al., "Cyanide toxicokinetics: the behavior of cyanide, thiocyanate and 2-amino-2-thiazoline-4-carboxylic acid in multiple animal models," Journal of Analytical Toxicology, vol. 38, No. 4, pp. 218-225 (2014).
Bizikova, P., et al., "Cloning and establishment of canine desmocollin-1 as a major autoantigen in canine pemphisgus foliaceus," Veterinary Immunology & Immunopathology, vol. 149, pp. 197-207 (2012).
Bizikova, P., et al., "Serum autoantibody profiles of IgA, IgE and IgM in canine pemphigus foliaceus," Veterinary Dermatology, vol. 25, pp. 471-475 (2014).
Bolon, B., et al., "STP Position Paper: Recommended Practices for Sampling and Processing the Nervous System (Brain, Spinal Cord, Nerve, and Eye) during Nonclinical General Toxicity Studies," Toxicologic Pathology, vol. 41, pp. 1028-1048 (2013).
Borthakur, G., et al., "Immune anaemias in patients with chronic lymphocytic leukaemia treated with fludarabine, cyclophosphamide and rituximab—incidence and predictors," British Journal of Haematology, vol. 136, No. 6, pp. 800-805 (2007).
Bradshaw, J., et al., "Prolonged and tunable residence time using reversible covalent kinase inhibitors," Nat Chem. Biol., 11 :525-531 (with online methods) (2015).
Brodsky, R.A., "Warm Autoimmune Hemolytic Anemia," New England Journal of Medicine, vol. 381, No. 7, pp. 647-654 (2019).
Brown, J.R., et al., "Phase I study of single-agent CC-292, a highly selective Bruton's tyrosine kinase inhibitor, in relapsed/refractory chronic lymphocytic leukemia," Haematologica, vol. 101, page e295 (2016).
Burchat, A., et al., "Pyrrolo[2,3-d]pyrimidines Containing an Extended 5-Substituent as Potent and Selective Inhibitors of Ick II," Bioorg. Med. Chem. Lett, 10:2171-2174 (2000).
Burger, J., "Bruton Tyrosine Kinase Inhibitors: Present and Future," Cancer Journal, vol. 25, No. 6, pp. 386-393 (2019).
Burger, J., et al., "Randomized Trial of Ibrutinib Versus Ibrutinib Plus Rituximab (Ib+R) in Patients with Chronic Lymphocytic Leukemia (CLL)," Blood, vol. 130, p. 427 (2019).
Burini, E., et al., "Efficient Synthesis of 4-Cyano 2,3-Dihydrooxazoles by Direct Amination of 2-Alkylidene 3-Oxo Nitriles," Synlett, 17: 2673-2675 (2005).
Bussel, J., et al., "A randomized, double-blind study of romiplostim to determine its safety and efficacy in children with immune thrombocytopenia," Blood, vol. 118, No. 1, pp. 28-36 (2011).
Bussel, J., et al., "Eltrombopag for the treatment of chronic idiopathic thrombocytopeniarpura," New England Journal of Medicine, vol. 357, pp. 2237-2247 (2007).
Butt, M., et al., "Nervous System: Astrocytosis," In Toxicologic Pathology Nonclinical Safety Assessment, Sahota, P. S., Popp, J.A., Hardistry, J.F., and Gopinath, C. (eds), vol. 20, pp. 901-903 (2013).
Byrd, J., et al., "Acalabrutinib (ACP-196) in relapsed chronic lymphocytic leukemia," New England Journal of Medicine, vol. 374, No. 4, pp. 323-332 (2016).
Caira, M., et al., "Crystalline Polymorphism of Organic Compounds," Topics in Current Chemistry, vol. 198, pp. 163-208 (1998).
Calderwood, D., et al., "Pyrrolo[2,3-d]pyrimidines Containing Diverse N-7 Substituents as Potent Inhibitors ofLck," Bioorg. Med. Chem. Lett., 12:1683-1686 (2002).
Carnero-Contentti, E., et al., "Bruton's tyrosine kinase inhibitors: a promising emerging treatment option for multiple sclerosis," Expert Opinion on Emerging Drugs, vol. 25, No. 4, pp. 377-381 (2020).
Carruthers, M., et al., "Development of an IgG4-RD Responder Index," International Journal of Rheumatology, vol. 2012, pp. 1-8 (2012).
CAS RN 26272-41-3, STN entered Nov. 16, 1984 (1 page).
Certified English Translation of CN 105753863 A published in Chinese on Jul. 13, 2016 (57 pages).
Chandler, J., et al., "Biochemical Mechanisms and Therapeutic Potential of the Pseudohalide Thiocyanate in Human Health," Free Radical Research, vol. 49, No. 6, pp. 695-710 (2015).
Chang, B., et al., "The Bruton tyrosine kinase inhibitor PCI-32765 ameliorites autoimmune arthritis by inhibition of multiple effector cells," Arthritis Research & Therapy, vol. 13, No. 4, p. R115 (2011).
Chaplin, H., Jr., "Clinical usefulness of specific antiglobulin reagents in autoimmune hemolytic anemias," Hematology Program, vol. 8, pp. 25-49 (1973).
Gao, Y., et al., "Hormones and diet, but not body weight, control hypothalamic microglial activity," Glia, vol. 62, pp. 17-25 (2014).
Garvin, C., "The Fatal Toxic Manifestations of the Thiocyanates," Journal of American Medical Association, vol. 112, No. 12, pp. 1125-1127 (1939).
Ghoreschi, K., et al., "Janus kinases i1 immune cell signaling," Immunol Rev., 228:273-287 (2009).
Ghoroi, C., et al., "Multi-faceted characterization of pharmaceutical powders to discern the influence of surface modification", Powder Technology, vol. 236, May 22, 2012, pp. 63-74.
Goldmann, L., et al., "Oral Bruton tyrosine kinase inhibitors block activation of the platelet Fc receptor CD32a (FcgRIIA): a new option in HIT?," Blood Advances, vol. 3, No. 23, pp. 4021-4033 (2020).

(56) References Cited

OTHER PUBLICATIONS

Goodman, T., et al., "Hypothalamic tanycytes—masters and servants of metabolic, neuroendocrine, and neurogenic functions," Frontiers in Neuroscience, vol. 9, p. 387 (2015).
Gordon, R., et al., "Inflammasome inhibition prevents alpha-synuclein pathology and dopaminergic neurodegeneration in mice," Science Translational Medicine, vol. 10, No. 465, p. eaah4066 (2018).
Grando, S. "Pemphigus autoimmunity: Hypotheses and realities," Autoimmunity, 45(1):7-35 (2012).
GRAS notification for sodium thiocyanate for use in the lactoperoxidase system, https://www.fda.gov/files/food/published/GRAS-Notice-GRN-753.pdf, Dec. 18, 2017.
Gregoriou, S., et al., "Management of pemphigus vulgaris: challenges and solutions," Clinical, Cosmetic & Investigational Dermatology, vol. 8, pp. 521-527 (2015).
Gyoung, Y., et al., "Regiospecific synthesis of 2-allylated-5-substituted tetrazoles via palladium-catalyzed reaction of nitriles, trimethylsilyl azide, and allyl acetates," Tetrahedron Lett., 41 (21): 4193-4196 (2000).
Hackam, D., et al., "Translation of Research Evidence from Animals to Humans," JAMA, 296(14):1731-1732 (2006).
Hantschel, O., et al., "The Btk tyrosine kinase is a major target of the Bcr-Abl inhibitor dasatinib." PNAS, 104(33):13283-13288 (2007).
Heneka, M., et al., "NLRP3 is activated in Alzheimer's disease and contributes to pathology in APP/PS1 mice," Nature, vol. 492, No. 7434, pp. 674-678 (2013).
Hertl, M., et al., "Pemphigus. S2 Guideline for diagnosis and treatment—guided by the European Dermatology Forum (EDF) in cooperation with the European Academy of Dermatology and Venereology (EADV)," Journal of the European Academy of Dermatology and Venereology, vol. 29, No. 3, pp. 405-414 (2015).
Hill, Q., et al., "The diagnosis and management of primary autoimmune haemolytic anaemia," British Journal of Haematology, vol. 176, No. 3, pp. 395-411 (2017).
Hodgson, K., et al., "Autoimmune cytopenia in chronic lymphocytic leukemia: diagnosis and treatment," British Journal of Haematology, vol. 154, No. 1, pp. 14-22 (2011).
Honigberg, L.A., et al., "The Bruton tyrosine kinase inhibitor PCT-32765 blocks B-cell activation and is efficacious in models of autoimmune disease and B-cell malignancy," PNAS, vol. 107, pp. 13075-13080 (2010).
Horvath, B., et al., "Low dose rituximab is effective in pemphigus," British Journal of Dermatology, vol. 166, No. 2, pp. 405-412 (2012).
Hu, C., "Production and Application of a Pharmaceutical Excipient—Thin Film Coating," Beijing: China Medical Science Press, p. 14 (May 31, 2014).
Hu, R., "Industrial Pharmaceutics," Beijing: China Press of Traditional Chinese Medicine, pp. 237-239 (Jul. 31, 2010).
Hutcheson, J., et al., "Modulating proximal cell signaling by targeting Btk ameliorates humoral autoimmunity and end-organ disease in murine lupus," Arthritis Research & Therapy, vol. 14, pp. R243 (2012).
Ihrke, P.J., et al., "Pemphigus foliaceus in dogs: a review of 37 cases," Journal of the American Veterinary Medical Association, vol. 186, No. 1, pp. 59-66 (1985).
International Preliminary Report on Patentability for International Application No. PCT/US2010/056890, mailed May 22, 2012, by P. Becamel (10 pages).
International Preliminary Report on Patentability for International Application No. PCT/US2021/012211, mailed on Jul. 21, 2022, by X. Wang (11 pages).
International Preliminary Report on Patentability for International Application No. PCT/US2021/014371, mailed Aug. 4, 2022, by S. Baharlou (7 pages).
International Preliminary Report on Patentability for International Application No. PCT/US2022/024806, mailed Oct. 26, 2023, by X. Tang (8 pages).
International Search Report and Written Opinion for International Application No. PCT/US2010/056890, mailed Jul. 28, 2011, by S. Lee (16 pages).
International Search Report and Written Opinion for International Application No. PCT/US2012/038092, mailed Jul. 5, 2012, by A. Schmid (8 pages).
International Search Report and Written Opinion for International Application No. PCT/US2012/038120, mailed Aug. 20, 2012, by I. Helps (10 pages).
International Search Report and Written Opinion for International Application No. PCT/US2012/038135, mailed Jul. 25, 2012, by I. Helps (9 pages).
International Search Report and Written Opinion for International Application No. PCT/US2012/038163, mailed Jul. 9, 2012, by A. Schmid (8 pages).
International Search Report and Written Opinion for International Application No. PCT/US2012/038214, mailed Feb. 1, 2013, by Y. Kim (12 pages).
International Search Report and Written Opinion for International Application No. PCT/US2013/045266, mailed Sep. 3, 2013, by W. Hoepfner (11 pages).
International Search Report and Written Opinion for International Application No. PCT/US2013/047958, mailed Oct. 1, 2013, by S. Gomez Gallardo (14 pages).
International Search Report and Written Opinion for International Application No. PCT/US2013/053042, mailed Nov. 18, 2013, by M. Kollmannsberger (12 pages).
International Search Report and Written Opinion for International Application No. PCT/US2013/058614, mailed Nov. 5, 2013, by C. Ladenburger (11 pages).
International Search Report and Written Opinion for International Application No. PCT/US2015/000303, mailed Mar. 21, 2016, by J. Konter (12 pages).
International Search Report and Written Opinion for International Application No. PCT/US2015/000515, mailed Apr. 18, 2016, by M. Kollmannsberger (11 pages).
International Search Report and Written Opinion for International Application No. PCT/US2015/016963, mailed Apr. 22, 2015, by T. Albayrak (10 pages).
International Search Report and Written Opinion for International Application No. PCT/US2015/066868, mailed Mar. 9, 2016, by S. Allnutt (13 pages).
International Search Report and Written Opinion for International Application No. PCT/US2016/035588, mailed Aug. 16, 2016, by W. Hoepfner (10 pages).
International Search Report and Written Opinion for International Application No. PCT/US2016/039070, mailed Oct. 6, 2016, by R. Saez Diaz (18 pages).
International Search Report and Written Opinion for International Application No. PCT/US2017/040075, mailed Oct. 2, 2017, by M. Ceyte (9 pages).
International Search Report and Written Opinion for International Application No. PCT/US2020/054809 mailed Jan. 25, 2021, by S. Collins (12 pages).
International Search Report and Written Opinion for International Application No. PCT/US2020/055410 mailed on Jan. 15, 2021, by A. Jakobs (8 pages).
International Search Report and Written Opinion for International Application No. PCT/US2020/065689, mailed on Apr. 29, 2021, by J. Guspanova (17 pages).
International Search Report and Written Opinion for International Application No. PCT/US2021/012211 mailed on Apr. 9, 2021, by B. Megido (13 pages).
International Search Report and Written Opinion for International Application No. PCT/US2021/014371, mailed Mar. 22, 2021, by S. Bissmire (14 pages).
International Search Report and Written Opinion for International Application No. PCT/US2022/024806, mailed Jul. 21, 2022, by M. Rodriguez-Palmero (12 pages).
Aaltonen, J., et al., "Solid form screening—A review," European Journal of Pharmaceutics and Biopharmaceutics, vol. 71, No. 1, pp. 23-37 (2009).

(56) References Cited

OTHER PUBLICATIONS

Anonymous, "Amorphous (E)-2-[3R)-3-[4-amino-3-(2-fluoro-4-phenoxyphenyl)pyrozolo[3,4-d]pyrimidin-1-yl] piperidine-1-carbonyl]-4-methyl-4-[4-oxetan-3-yl)piperazin-1-yl]pent-2-enenitrile and amorphous salts thereof," https://priorart.ip.com/IPCOM/00026458 (Jan. 11, 2021).
Anonymous: "Ibrutinib and Acalabrutinib for COVID-19," CLL Society, URL:https://cllsociety.org/2020/04/ibrutinib-and-acalabrutinib-for-covid-19/, pp. 1-4 (2020).
Anonymous: "Proof of Concept Study of Rilzabrutinib in Adult Participants with Moderate-to-severe Asthma—NCT05104892," ClinicalTrials.gov, (Dec. 12, 2021).
Ashizawa, K., Crystallization of Pharmaceuticals and Chemistry of Polymorphic Phenomena, pp. 273, 278, 305-317 (2002).
Astrazeneca: "AstraZeneca initiates CALAVI clinical trial with Calquence against COVID-19," (2020).
Braga, D., et al., "Crystal Polymorphism and multiple crystal forms," Structure and Bonding, vol. 132, pp. 25-50 (2009).
Byrn, S., et al., "Pharmaceutical Solids: A Strategic Approach to Regulatory Considerations," Review, Pharmaceutical Research, vol. 12, No. 7, pp. 945-954 (1995).
DePorto, A., et al., "BTK inhibitor ibrutinib reduces inflammatory myeloid cell responses in the lung during murine pneumococcal pneumonia," Molecular Medicine, vol. 25, No. 1 (2019).
Feng, Y., et al., "Bruton's tyrosine kinase (BTK) inhibitors in treating cancer: a patent review (2010-2018)," Expert Opinion on Therapeutic Patents, 29:4, 217-241 (2019).
Florence, J., et al., "Inhibiting Bruton's tyrosine kinase rescues mice from lethal influenze-induced acute lung injury," American Journal of Physiology, vol. 315, No. 1, pp. 52-58 (2018).
Herter, J., et al., "PRN473, an inhibitor of Bruton's tyrosine kinase, inhibits neutrophil recruitment via inhibition of macrophage antigen-1 signalling: PRN473 inhibits PMN influx by blocking Mac-1 signalling," British Journal of Pharmacology, vol. 175, No. 3, pp. 429-439 (2018).
Hilfiker, R., et al., "Relevance of solid-state properties for pharmaceutical products," Polymorphism: in the Pharmaceutical Industry, pp. 1-19 (2006).
Kolkhir, P., et al., "Urticaria," Nature Reviews Disease Primers, vol. 8, No. 1, (2022).
Krupa, A., et al., "Bruton's Tyrosine Kinase Mediates Fc[gamma]Rlla/Toll-Like Receptor-4 Receptor Crosstalk in Human Neutrophils," American Journal of Respiratory Cell and Molecular Biology, vol. 48, No. 2, pp. 240-249 (2013).
Krupa, A., et al., "Silencing Bruton's tyrosine kinase in alveolar neutrophils protects mice from LPS/immune complex-induced acute lung injury," American Journal of Physiology, vol. 307, No. 6, pp. 435-448 (2014).
Kurdowska, A., et al., "Therapeutic Targeting of Bruton's Kinase for the Treatment of Acute Lung Injury," A45. Critical Care: Of Mice and Men, Insights from Experimental and Animal Models in ARDS and Sepsis, p. A1695 (2019).
Lever, W., et al., "Immunosuppressants and Prednisone in Pemphigus Vulgaris, " Archives of Dermatology, vol. 113, pp. 1236-1241 (1977).
Long et al., "AB0756□Immune-Mediated Basis for a Phase 2A Clinical Study Comparing Rilzabrutinib Vs Glucocorticoids in Rituximab-Refractory Patients With IGG4-Related Disease", Annals of the Rheumatic Diseases, 80:1406 (2021).
Metz, M., "Treatments for chronic pruritus outside of the box", Experimental Dermatology, vol. 28, No. 12, pp. 1476-1481 (2019).
Nadeem, A., et al., "Bruton's tyrosine kinase inhibition attenuates oxidative stress in systemic immune cells and renal compartment during sepsis-induced acute kidney injury in mice," International Immunopharmacology, vol. 90, p. 107123 (2021).
Owens, T., et al., "Discovery of Reversible Covalent Bruton's Tyrosine Kinase Inhibitors PRN473 and PRN1008 (Rilzabrutinib)," Journal of Medicinal Chemistry, vol. 65, No. 7, pp. 5300-5316 (2022).
Roschewski, M., et al., "Inhibition of Bruton tyrosine kinase in patients with severe COVID-19," Science Immunology, vol. 5, No. 48, page eabd0110 (2020).
Rosenbach, M., et al., "Reliability and convergent validity of two outcome instruments for pemphigus," Journal of Investigative Dermatology, vol. 29, No. 10, pp. 2404-2410 (2009).
Ruella, M., et al., "Kinase inhibitor ibrutinib to prevent cytokine-release syndrome after anti-CD19 chimeric antigen receptor T cells (CART) for B cell neoplasms," Leukemia, (2016).
Sarma, B., et al., "Solid formation of pharmaceuticals: Polymorphs, salt and cocrystals," Korean Journal of Chemical Engineering, vol. 28, No. 2, pp. 315-322 (2011).
Treon, S., et al., "The BTK inhibitor ibrutinib may protect against pulmonary injury in COVID-19-infected patients," Blood, American Society of Hematology, vol. 135, No. 21, pp. 1912-1915 (2020).
Zhou, P., et al., "Knockdown of Bruton's tyrosine kinase confers potent protection against sepsis-induced acute lung injury," Cell Biochemistry and Biophysics, vol. 70, No. 2, pp. 1265-1275 (2014).
International Search Report and Written Opinion for International Application No. PCT/US2023/078211 dated Feb. 12, 2024, by N. Hick (13 pages).
International Search Report and Written Opinion for International Application No. PCT/US2023/083090, mailed on Apr. 30, 2024, by I. Estanol (12 pages).
Irwin, S., "Comprehensive observational assessment: la. A systematic, quantitative procedure for assessing the behavioral and physiologic state of the mouse," Psychopharmacologia, vol. 13, No. 3, pp. 222-257 (1968).
Ito, M., et al., "Bruton's tyrosine kinase is essential for NLRP3 inflammasome activation and contributes to ischaemic brain injury," Nature Communications, vol. 6, No. 1, p. 1 (2015).
Ivankovic, S., Fehlende teratogene Wirkung von Nitroprussidnatrium (NNP) an Wistar-Ratten und Kaninchen [Absence of a teratogenic effect of sodium nitroprusside in wistar rats and rabbits (author's transl)]. Arzneimittelforschung, vol. 29, No. 8, pp. 1092-1094 (1979).
Izumi, K. et al., "Current Clinical Trials in Pemphigus and Pemphigoid", Frontiers in Immunology, vol. 10, p. 978 (May 3, 2019).
Jager, U., et al., "Diagnosis and treatment of autoimmune hemolytic anemia in adults: Recommendations from the First International Consensus Meeting," Blood Review, vol. 41, p. 100648 (2020).
Jenner, G., "Steric effects i1 high pressure Knoevenagel reactions," Tetrahedron Lett., 42(2): 243-245 (2001).
Liu, J., et al., "Emerging small-molecule inhibitors of the Bruton's tyrosine kinase (BTK): Current development", European Journal of Medicinal Chemistry, vol. 217, Mar. 12, 2021, p. 113329.
Johnson, M., et al., "Coding for Dry Eye," Optometric Management, Issue: Mar. 2004 (1 page).
Joly, P., et al., "First-line rituximab combined with short-term prednisone versus prednisone alone for the treatment of pemphigus (Ritux 3): a prospective, multicentre, parallel-group, open-label randomised trial," Lancet, vol. 389, No. 10083, pp. 2031-2040 (2017).
Joly, P., et al., "Pemphigus group (vulgaris, vegetans, foliaceus, herpetiformis, brasiliensis)," Clinical Dermatology, vol. 29, No. 4, pp. 432-436 (2011).
Jordan, V., "Tamoxifen: A Most Unlikely Pioneering Medicine," Nat Rev. Drug Discov., 2:205-213 (2003).
Kamaly, N., et al., "Degradable Controlled-Release Polymers and Polymeric Nanparticles: Mechanisms of Controlling Drug Release," Chemical Reviews, vol. 116, pp. 2602-2663 (Feb. 8, 2016).
Kamath, S., et al., "Receptor-Guided Alignment-Based Comparative 3D-QSAR Studies of Benzylidene Malonitrile Tyrphostins as EGFR and HER-2 Kinase Inhibitors," J Med. Chem., 46:4657-4668 (2003).
Kamijo, S., et al., "Tetrazole synthesis via the palladium-catalyzed three component coupling reaction," MolecularDiversitY, 6: 181-192 (2003).
Kanwar, A., et al., "Rituximab i1 Pemphigus," Indian J Dermatol. Venereal. Leprol. [serial online], 78:671-676 (2012).
Karra, E., et al., "The role of peptide YY in appetite regulation and obesity," Journal of Physiology, vol. 587, No. 1, pp. 19-25 (2009).

(56) References Cited

OTHER PUBLICATIONS

Khellaf, M., et al., "Safety and efficacy of rituximab in adult immune thrombocytopenia: results from a prospective registry including 248 patients," Blood, vol. 124, No. 22, pp. 3228-3236 (2014).
Khosroshani, A., et al., "Rituximab for the treatment of lgG4-Related Disease," Medicine, vol. 91, pp. 57-66 (2012).
Kihlman, B., "Experimentally Induced Chromosome Aberrations in Plants, I. The production of chromosome aberrations by cyanide and other heavy metal complexing agents," Journal of Biophysical & Biochemical Cytology, vol. 3, No. 3, pp. 363-380 (1957).
Kim, K., et al., "Imidazo[1.5-a]quinoxalines as irreversible BTK inhibitors for the treatment of rheumatoid arthritis," Bioorganic & Medicinal Chemical Letters, vol. 21, pp. 6258-6263 (2011).
Klein, N., et al., "Rates of autoimmune diseases in Kaiser Permanente for use in vaccine adverse event safety studies," Vaccine, vol. 28, No. 4, pp. 1062-1068 (2010).
Knight, Z., et al., "A membrane capture assay for lipid kinase activity," Nat Protoc., 2(10):2459-2466 (2017).
Kohrt, H., et al., "Ibrutinib antagonizes rituximab-dependent NK cell-mediated cytotoxicity," Blood, vol. 123, No. 12, pp. 1957-1960 (2014).
Kojima, S., et al. "Stereoselective synthesis of activated cyclopropanes with an a-pyridinium acetamide bearing an 8-phenylmenthyl group as thechiral auxiliary," Tetrahedron Lett., 45(18): 3565-3568 (2004).
Komura, K., et al., "Layered silicate PLS-1: A new solid base catalyst for C—C bond forming reactions," Cata! Commun., 8(4): 644-648 (2007).
Kotz, A., et al., "The Action of Chloroform on Methylene and Metheny! Groups," Journal fuer Praktische Chemie (Leipzig), Abstract, 74: 425-48 (1907).
Kridin, K., et al., "Mortality and Cause of Death in Patients with Pemphigus," Acta Dermato-Venereologica, vol. 97, No. 5, pp. 607-611 (2017).
Kuter, D., et al., "22 oral rilzabrutinib Bruton tyrosine kinase inhibitor, showed clinically active and durable platelet responses and was well-tolerated in patients with heavily pretreated immune thrombocytopenia," 62nd ASH Annual Meeting & Exposition, Abstract (presentation) (Dec. 5-8, 2020).
Kuter, D., et al., "LUNA3 Phase III Multicenter, Double-Blind, Randomized, Placebo-Controlled Trial of the Oral BTK Inhibitor Rilzabrutinib in Adults and Adolescents with Persistent or Chronic Immune Thrombocytopenia," Blood, vol. 138, supplement 1, p. 1010 (2021).
Kuter, D., et al., "Phase I/II, open-label, adaptive study of oral tyrosine inhibitor patients with relapsed/refractory primary or secondary immune thrombodytopenia," Blood, vol. 134 (Suppl 1), p. 87 (2019).
Kuter, D., et al., "Rilzabrutinib versus placebo in adults and adolescents with persistent or chronic immune thrombocytopenia: LUNA3 phase III study," Therapeutic Advances in Hematology, vol. 14, pp. 1-14 (2023).
Kuter, D., et al., "Rilzabrutinib, an Oral BTK Inhibitor, in Immune Thrombocytopenia," MEJM Paper, vol. 386, No. 15, pp. 1421-1431 (2022).
Kuter, D., et al., "Safety and efficacy of rilzabrutinib (PRN1008), an oral Bruton tyrosine kinase inhibitor, in relapsed/refractory patients with primary or secondary immune thrombocytopenia: Phase I/II adaptive study," European Hematology Association (EHA) annual meeting, vol. 4, No. S1, pp. 118-119 (abstract S316) poster presentation (2020).
Langrish, C., et al., Preclinical Efficacy and Anti-Inflammatory Mechanisms of Action of the Bruton Tyrosine Kinase Inhibitor Rilzabrutinib for Immune-Mediated Disease, Journal of Immunology, vol. 206, No. 7, pp. 1454-1486 (2021).
Langrish, C., et al., "PRN1008, a Reversible Covalent BTK Inhibitor in Clinical Development for Immune Thrombocytopenia Purpura," Blood, vol. 130, suppl. 1, No. 1052 (2017).
Leopold, C., "A Practical Approach in the Design of Colon-specific Drug Delivery System," Wiley-VCH; Drug Targeting Organ-Specific Strategies, Chapter 6, pp. 157-170 (2001).
Zhensu, L., Medicinal Chemistry, Chemical Industry Press, China, Mar. 3, 1981, pp. 435-436.
Liang, C., et al., "The development of Bruton's tyrosine kinase (BTK) inhibitors from 2012 to 2017: A mini-review," European Journal of Medicinal Chemistry, vol. 151, pp. 315-326 (2018).
Lindberg, H., et al., "Observations of the Pathologic Effects of Thiocyanate: An Experimental Study," American Heart Journal, vol. 21, No. 5, pp. 605-616 (1941).
Lipsky, A., et al., Managing toxicities of Bruton tyrosine kinase inhibitors, Hematology, American Society of Hematology Education Program, vol. 2020, No. 1, pp. 336-345 (2020).
Lou, Y., et al., "Bruton's Tyrosine Kinase Inhibitors: Approaches to Potent and Selective Inhibition, Preclinical and Clinical Evaluation for Inflammatory Diseases and B Cell Malignancies," J Med. Chem., 55(10): 4539-4550 (2012).
Maas, S., et al., "Conjugate Addition of Dialkylaluminum Chlorides to Alkylidenemalonic Acid Derivatives," Synthesis, vol. 10, pp. 1792-1798 (1999).
Mahajan, V., et al., "lgG4-Related Disease," Annual Review of Pathology: Mechanisms of Disease, vol. 9, pp. 315-347 (2014).
Mahoney, M., et al., "Explanations for the clinical and microscopic localization of lesions in pemphigus foliaceus and vulgaris," Journal of Clinical Investigation, vol. 103, No. 4, pp. 461-468 (1999).
Maronpot, R., et al., "Hepatic Enzyme Induction: Histopathology," Toxicologic Pathology, vol. 38, pp. 776-795 (2010).
Martin, Y., et al., "Do structurally similar molecules have similar biological activity?," Journal of Medicinal Chemistry, vol. 45, No. 19, pp. 4350-4538 (2002).
Masters, S., et al., "Activation of the NLRP3 inflammasome by islet amyloid polypeptide provides a mechanism for enhanced IL-1Beta in type 2 diabetes," Nature Immunology, vol. 11, No. 10, pp. 897-904 (2010).
Maurya, R., et al., "Catalyst-free stereoselective cyclopropanation of electron deficient alkenes with ethyl diazoacetate," RSC Advances, vol. 3, pp. 15600-15603 (2013).
A Study of PRN1008 in Adult Patients With Pemphigus Vulgaris. Mar. 4, 2016.
Anonymous, "Application No. 214783Orig1s000: Multi-discipline review Summary Review Clinical Review Non-Clinical Review Statistical Review Clinical Pharmacology Review", Internet: URL;https://www.accessdata.fda.gov/drugsatfda_docs/nda/2021/214783Orig1s000MultidisciplineR.pdf, Feb. 20, 2023.
Anonymous: An Adaptive, Open-Label, Dose-Finding, Phase 1/2 Study Investigating the Safety, Pharmacokinetics, and Clinical Activity of PRN1008, an Oral BTK Inhibitor, in Patients With Relapsed Immune Thrombocytopeni Purpura, https://clinicaltrials.gov/study/NCT03395210?term=NCT03395210&rank=1&tab=history&a=8#version-content-panel, Oct. 2, 2019.
Bernstein, J., "Polymorphism molecular crystals" Moscow, Science, 2007, ch. 7.7. Importance amorphous forms, pp. 337-339 (2007) (with English translation) (11 pages).
Bernstein, Johnathan A., et al., "BTK signaling-a crucial link in the pathophysiology of chronic spontaneous urticaria", J. of Allergy and Clinical Immunology, vol. 153, No. 5, pp. 1229-1240, (2023).
Brittain, H. G., Polymorphism in pharmaceutical solids, Marcel Dekker, Inc. (1999).
Cao, et al., "Remdesivir for severe acute respiratory syndrome coronavirus 2 causing COVID-19: An evaluation of the evidence", Travel Medicine and Infectious Disease, 35, pp. 101647 (2020).
ClinicalTrial.gov ID No. NCT05002777, "Efficacy, Safety and Pharmacokinetics of Rilzabrutinib in Patients With Warm Autoimmune Hemolytic Anemia (wAIHA)(LUMINA 2)", last update posted May 21, 2025 (15 pages).
Communication Pursuant to Article 94(3) EPC for European Patent Application No. 13731218.7, mailed Sep. 23, 2015.
Cooper et al., "Efficacy and Safety Results With Rilzabrutinib, an Oral Bruton Tyrosine Kinase Inhibitor, in Patients With Immune Thrombocytopenia: Phase 2 Part B Study," American Journal of Hematology, 100, pp. 439-449 (2025).

(56) References Cited

OTHER PUBLICATIONS

Daak, A.et al.,: "Bruton Tyrosine Kinase Inhibitor Rilzabrutinib Reduces Vasa-Occlusion and Markers of Inflammation and Adhesion in Transgenic Mice with Sickle Cell Disease", Blood, vol. 144, No. supplement 1, pp. 2482-2483 (2024).
Dispenza, M.C., "The Use of Bruton's Tyrosine Kinase Inhibitors to Treat Allergic Disorders," Current Treatment Options in Allergy, vol. 8, No. 3, pp. 261-273 (2021).
Extended European Search Report for European Patent Application No. 17152898.7, dated Mar. 8, 2017.
Global News Wire: "Principia Biopharma Reports Positive PRN1008 Phase 2 Top-Line Results and Initiates Phase 3 Pemphigus Program", https://www.globenewswire.com/news-release/2018/11/29/1659390/0/en/Principia-BiopharmaReports-Positive-PRN1008-Phase-2-Top-Line-Results-and-Initiates-Phase-3-PemphigusProgram.html (Nov. 29, 2018).
Hancock et al., "Characteristics and Significance of the Amorphous State in Pharmaceutical Systems," Journal of Pharmaceutical Sciences, 86(1), pp. 1-12 (1997).
Huijbers et al., "lgG4-mediated autoimmune diseases: a niche of antibody-mediated disorders", Ann. N.Y. Acad. Sci, 1413, pp. 92-103 (2018).
International Preliminary Report on Patentability for International Application No. PCT/US2013/058614, mailed Nov. 19, 2013, by Y. Nakamura (15 pages).
International Preliminary Report on Patentability for International Application No. PCT/US2015/000303, mailed Jun. 27, 2017, by L. Bai (18 pages).
International Preliminary Report on Patentability for International Application No. PCT/US2015/016963, mailed Aug. 23, 2026, by S. Baharlou (9 pages).
International Preliminary Report on Patentability for International Application No. PCT/US2017/040075, mailed Jan. 1, 2019, by A. Nickitas-Etienne (15 pages).
International Preliminary Report on Patentability for International Application No. PCT/US2020/054809, mailed Apr. 12, 2022, by X. Wang (9 pages).
International Preliminary Report on Patentability for International Application No. PCT/US2020/065689, mailed on May 17, 2022, by A. Nickitas-Etienne (12 pages).
International Preliminary Report on Patentability for International Application No. PCT/US2021/028381 mailed Nov. 3, 2022, by F. Doherty (14 pages).
International Preliminary Report on Patentability for International Application No. PCT/US2023/025124, mailed on Dec. 10, 2024, by F. Doherty (10 pages).
International Preliminary Report on Patentability for International Application No. PCT/US2023/078211, mailed on Apr. 29, 2025, by X. Wang (8 pages).
International Preliminary Report on Patentability for International Application No. PCT/US2023/083090, mailed on Jun. 10, 2025, by F. Doherty (9 pages).
International Search Report and Written Opinion for International Application No. PCT/US2021/028381, mailed Aug. 3, 2021, by Brell, E., (10 pages).
International Search Report and Written Opinion for International Application No. PCT/US2023/025124, mailed Sep. 6, 2023, by A. Pfau, (16 pages).
International Search Report and Written Opinion for International Application No. PCT/US2024/035719; dated Feb. 14, 2025, by U. Haider, (14 pages).
International Search Report and Written Opinion for International Application No. PCT/US2024/040259, mailed Jan. 28, 2025, E. Baston, (21 pages).
International Search Report and Written Opinion for International Application No. PCT/US2024/052716, mailed Feb. 17, 2025, by A. Rinck (15 pages).
International Search Report and Written Opinion for International Application No. PCT/US2024/052717, mailed Jan. 23, 2025, by S. Collins, (12 pages).
International Search Report and Written Opinion for International Application No. PCT/US2024/058667, mailed Mar. 28, 2025, by M. Hortner (11 pages).
International Search Report and Written Opinion for International Application No. PCT/US2025/020419; dated Jun. 26, 2025, by N. Leitner, (12 pages).
International Search Report and Written Opinion for International Application No. PCT/US2025/038731, mailed Nov. 24, 2025, by C. Bonzano (14 pages).
International Search Report and Written Opinion for International Application No. PCT/US2025/038928, mailed Nov. 25, 2025, by C. Bonzano (14 pages).
International Search Report and Written Opinion for International Application No. PCT/US2025/040860, mailed Nov. 18, 2025, by P. Opravz (15 pages).
Kashiwagi, H., "New drugs for the treatment of primary immune thrombocytopenia", Rinsho Ketsueki, 65(9), pp. 1101-1105 (2024), doi: 10.11406/rinketsu.65.1101(with English abstract).
Kolkhir, P., et al., "Autoimmune chronic spontaneous urticaria," J. of Allergy and Clinical Immunology, vol. 146, No. 16, pp. 1819-1831 (2022).
Kümmerer, Klaus, "Pharmaceuticals in the Environment", Annu. Rev. Environ. Resour. 35, pp. 57-75 (2010).
Kuter et al., "Rilzabrutinib for immune thrombocytopenia", N. Engl. J. Med, 386, pp. 1421-1431 (2022).
Kuter, et al., "Long-term treatment with rilzabrutinib in patients with immune thrombocytopenia," Blood Advances vol. 8, No. 7, pp. 1715-1724 (2024).
Leitinger et al., "BTK Inhibitors in Haematology: Beyond B Cell Malignancies", Transfusion Medicine Reviews, 36, pp. 239-245 (2022).
Maurer, M., et al., "Efficacy and Safety of Rilzabrutinib in Patients With Chronic Spontaneous Urticaria; 12-Week Results from the RILECSU Phase 2 Dose-Ranging Study", Journal of Allergy and Clinical Immunology, vol. 153, No. 2, Abstract only (2024).
Meng et al., "The Role of CLEC-2 and Its Ligands in Thromboinflammation," Frontiers in Immunology vol. 12, article 688643, pp. 1-9 (2021).
Miller, J., et al., "Solvent Systems for Crystallization and Polymorph Selection," Chapter 3, Springer eBooks, pp. 53-109 (2007).
Morissette et al., "High-throughput crystallization: polymorphs, salts, co-crystals and solvates of pharmaceutical solids", Advanced Drug Delivery Reviews, 56(3), pp. 275-300 (Jan. 1, 2004).
Murrell et al., "Phase 2 Believe study part B: Efficacy and safety of rilzabrutinib for patients with pemphigus vulgaris", Jeadv, 36, pp e852-E855 (2022).
Nandiyanto et al., "Progress in developing spray-drying methods for the production of controlled morphology particles: From the nanometer to submicrometer size ranges," Advanced Powder Technology 22, pp. 1-19 (2011).
Pang, Y., et al., "The ISHLT chronic lung allograft dysfunction consensus criteria are applicable to pulmonary chronic graft-versus-host disease", Blood Advances, vol. 6, No. 14, pp. 4196-4207 (2022).
Chaudhri, O., et al., "Can Gut Hormones Control Appetite and Prevent Obesity?," Diabetes Care, vol. 31, pp. S284-S289 (2008).
Chen, J., et al., "The clinical significance of circulating B cells and secreting anti-glycoprotein IIb/IIIa antibody and platelet glycoprotein IIb/IIIa in patients with primary immune thrombocytopenia," Hematology, vol. 15, pp. 283-290 (2013).
Chinese Pharmacopoeia Commission, "The Third Supplement of the Pharmacopoeia of People's Republic of China (Edition 2010)," Beijing: China Medical Science Press, p. 213 (Nov. 30, 2014).
ClinicalTrial.gov ID No. NCT02704429, "A Study of PRN1008 in Adult Patients With Pemphigus Vulgaris", last update posted Feb. 13, 2023 (49 pages).
ClinicalTrial.gov ID No. NCT03395210, "A Study of Rilzabrutinib in Adult Patients With Immune Thrombocytopenia (ITP)", last update posted Jul. 28, 2023 (18 pages).
ClinicalTrial.gov ID No. NCT03762265, "A Study of PRN1008 in Patients With Pemphigus", last update posted Aug. 2, 2023 (104 pages).

(56) References Cited

OTHER PUBLICATIONS

ClinicalTrial.gov ID No. NCT04520451, "Open Label Two-Arm Study to Evaluate Rilzabrutinib in lgG4-Related Disease Patients", last update posted Sep. 7, 2023 (20 pages).
ClinicalTrial.gov ID No. NCT04562766, "Study to Evaluate Rilzabrutinib in Adults and Adolescents With Persistent or Chronic Immune Thrombocytopenia (ITP) (Luna 3)", last update posted Aug. 21, 2023 (24 pages).
ClinicalTrial.gov ID No. NCT04748926, "Food Effect and Relative Bioavailability Study of Rilzabrutinib in HealthyParticipants", last update posted Apr. 25, 2022 (20 pages).
ClinicalTrial.gov ID No. NCT05002777, "Efficacy, Safety and Pharmacokinetics of Rilzabrutinib in Patients With Warm Autoimmune Hemolytic Anemia (wAIHA)", last update posted Jul. 27, 2023 (20 pages).
ClinicalTrial.gov ID No. NCT05018806, "Proof of Concept Study of Rilzabrutinib in Adult Patients With Moderate-to-severe Atopic Dermatitis", last update posted Jul. 6, 2023 (23 pages).
ClinicalTrial.gov ID No. NCT05104892, "Proof of Concept Study of Rilzabrutinib in Adult Participants With Moderate-to-severe Asthma", last update posted Aug. 21, 2023 (25 pages).
ClinicalTrial.gov ID No. NCT05107115, "Rilzabrutinib for the Treatment of Chronic Spontaneous Urticaria in Patients Who Remain Symptomatic Despite the Use of H1 Antihistamine (RILECSU)", last update posted Aug. 24, 2023 (22 pages).
Code of Federal Regulations, Title 21, Chapter II, Part 1308, Schedules of Controlled Substances, Jan. 30, 2023.
Cohen, M., et al., "Structural Bioinformatics-Based Design of Selective, Irreversible Kinase Inhibitors," Science, 308:1318-1321 (2005).
Crowther, M., et al., "Evidence-based focused review of the treatment of idiopathic warm immune hemolytic anemia in adults," Blood, vol. 118, No. 15, pp. 4036-4040 (2011).
Cui, C., et al., "Factors Contributing to Drug Release From Enteric-Coated Omeprazole Capsules: An In Vitro and In Vivo Pharmacokinetic Study and IVIVC Evaluation in Beagle Dogs," Nanotechnology and Microtechnology in Drug Delivery Systems, vol. Jan.-Mar. 2020, pp. 1-13 (Jan. 7, 2020).
Cuker, A., et al., "How I treat refractory immune thrombocytopenia," Blood, vol. 128, No. 12, pp. 1547-1554, Sep. 22, 2016.
Database Biosis [Online], Biosciences Information Service, Kuter, D., et al., "Cognitive Impairment Among Patients with Chronic Immune Thromocytopenia," Blood, vol. 140, suppl. 1, pp. 8422-8424 (2022).
Database Biosis [Online], Biosciences Information Service, Langrish, C., et al., "PRN1008, a Reversible Covalent BTK Inhibitor in Cinical Development for Immune Thrombocytopenia Purpura," Blood, vol. 130, suppl. 1, p. 1052 (2017).
Database Embase [Online], Elsevier Science Publishers, Kuter, D., "Oral Rilzabrutinib, a Bruton Tyrosine Kinase Inhibitor, Showed Clinically Active and Durable Platelet Responses and Was Well-Tolerated in Patients with Heavily Pretreated Immune Thrombocytopenia," Blood, vol. 136, suppl. 1, pp. 20201205-20201208 (2020).
Database Embase [Online], Elsevier Science Publishers, Kuter, D., "Updated main study period and long-term extension (LTE) results with oral Bruton tyrosine kinase inhibitor rilzabrutinib in immune thrombocytopenia (ITP)," Research and Practice in Thrombosis and Haemostasis, vol. 6, suppl. 1 (2022).
Deng, Y., et al., "Reversible phospho-Smad3 signalling between tumour suppression and fibrocarcinogenesis i1 chronic hepatitis B infection," Clin. Exp. Immunol., 176:102-111 (2013).
DeSilva, A., et al., "Gut Hormones and Appetite Control: A Focus on PYY and GLP-1 as Therapeutic Targets in Obesity," Gut Liver, vol. 6, No. 1, pp. 10-20 (2012).
Dias, A., et al., "Ibrutinib: A New Frontier in the Treatment of Chronic Lymphocytic Leukemia by Bruton's Tyrosine Kinase Inhibition," Cardiovasc Hematol Agents Med Chem, 11 (4):265-271 (2013).
Dick, et al., "Pemphigus: A treatment update," Autoimmunity 2009, vol. 39, No. 7, pp. 591-599 (Jul. 7, 2009).
Dierickx, D., et al., "Rituximab in autoimmune haemolytic anaemia and immune thrombocytopenia purpura: a Belgian retrospective multicentric study," Journal of Internal Medicine, vol. 266, No. 5, pp. 484-491 (2009).
DiPaolo, J.A., et al., "Specific Btk inhibition suppresses B cell- and myeloid cell-mediated arthritis," Nature Chemical Biology, vol. 7, pp. 41-50 (2011).
Dispenza, M.C., et al., "Bruton's tyrosine kinase inhibition effectively protects against human lgE-mediated anaphylaxis," Journal of Clinical Investigation, vol. 130, No. 9, pp. 4759-4770 (2020).
Donald, A., et al., "Rapid Evolution of 6-Phenylpurine Inhibitors of Protein Kinase B through Structure-Based Design," J Med. Chem., 50:2289-2292 (2007).
Eaton, W., et al., "Epidemiology of autoimmune diseases in Denmark," Journal of Autoimmunity, vol. 29, No. 1, pp. 1-9 (2007).
Elinson, M., et al., "Electrochemical transformation of cyanoacetic ester and alkylidenecyanoacetic esters into 3-substituted 1,2-dicyanocyclopropane-1,2-dicarboxylates," Russian Chemical Bulletin, 47(6):1133-1136 (1998).
Elizondo-Vega, R., et al., "The role of tanycytes in hypothalamic glucosensing," Journal of Cellular and Molecular Medicine, vol. 19, pp. 1471-1482 (2015).
Elliott, M., et al., "Insecticidal activity of the Pyrethrins and Related Compounds x.• 5-Benzyl-3-furylmethyl 2,2-dimethylcyclopropanecarboxylates with ethylenic substituents at position 3 on the cyclopropane ring," Pestic. Sci., 7: 499-502 (1976).
Elliott, M., et al., "The Pyrethrins and Related Compounds. Part XVIII. Insecticidal 2,2-Dimethylcyclopropanecarboxylates with New Unsaturated 3-Substituents," Journal of the Chemical Society, Perkin Transactions 1: Organic and Bio-Organic Chemistry, vol. 21, 2470-2474 (1972-1999) (1974).
English Language Abstract for JP 42008308 B4, published Apr. 8, 1967, by Yoshitomi Pharmaceutical Industries, Ltd. (1 page).
English Translation of Office Action issued Apr. 12, 2013, in Chinese Application No. 201080061570.1.
EU Clinical Trials Register, ACT17125, Spain, first entered into EudraCT Dec. 20, 2022 (5 pages).
EU Clinical Trials Register, ACT17207, Germany, first entered into EudraCT Aug. 6, 2021 (5 pages).
EU Clinical Trials Register, ACT17208, Spain, first entered into EudraCT Aug. 5, 2021 (7 pages).
EU Clinical Trials Register, ACT17209, Spain, first entered into EudraCT Jun. 23, 2021 (6 pages).
EU Clinical Trials Register, DFI17124, Czech, first entered into EudraCT Dec. 12, 2017 (8 pages).
EU Clinical Trials Register, DRI17224, Spain, first entered into EudraCT Jul. 15, 2021 (6 pages).
EU Clinical Trials Register, EFC17092, Summary Results, Jul. 29, 2022 (9 pages).
EU Clinical Trials Register, EFC17093, Germany, first entered into EudraCT Oct. 1, 2020 (6 pages).
EU Clinical Trials Register, PRN1008-012, France, first entered into EudraCT Oct. 22, 2018 (6 pages).
Evans, E., et al., "Inhibition of Btk with CC-292 Provides Early Pharmacodynamic Assessment of Activity i1 Mice and Humans," J. Pharm. Exp. Ther., 346(2):219-28 (2013).
Fayyaz, A., et al., "Haematological manifestations of lupus," Lupus Science & Medicine, vol. 2, No. 1, p. e000078 (2015).
Fioravanti, S., et al., "Parallel Solution-Phase Synthesis of Acrylonitrile Scaffolds Carrying L-a-Amino Acidic or D-Glycosyl Residues," J Comb. Chem., 8: 808-811 (2006).
Futatani, T., et al., "Bruton's tyrosine kinase is present in normal platelets and its absence identifies patients with X-linked agammaglobulinaemia and carrier females," British Journal of Haematology, vol. 114, No. 1, pp. 141-149 (2001).
Bavin, M., "Polymorphism in Process Development", Chemistry and Industry, pp. 527-529, (1989).
Belikov, V.G., "Pharmaceutical Chemistry," textbook, 2007, Moscow, MEDpress-inform, pp. 27-29, with English translation of pp. 27-29; 10 pages.

(56) References Cited

OTHER PUBLICATIONS

Carlson et al., "An integrated high throughput workflow for pre-formulations: Polymorph and salt selection studies," Pharma Chem Drug Development, Jul./Aug. 2003, pp. 10-15.
Chappa et al., "Pharmaceutical Solid Form Screening and Selection: Which Form Emerges?" Cryst. Growth Des. 25, pp. 4783-4794 (2025).
Cooper et al., "Immune Thrombocytopenia", N Engl J Med, 381(10), pp. 945-955 (2019).
International Preliminary Report on Patentability for International Application No. PCT/US2024/035719, mailed Jan. 15, 2026, by S. Hwa Lee (10 pages).
International Preliminary Report on Patentability for International Application No. PCT/US2024/040259, mailed Feb. 12, 2026, by M. Kobayashi (14 pages).
Kwon et al. "Spray-Dried Amorphous Solid Dispersions of Atorvastatin Calcium for Improved Supersaturation and Oral Bioavailability," Pharmaceutics (11)(461); pp. 1-13 (2019).
Manu et al., "Spray Drying in Pharmaceutical Industry: A Review," Research J. Pharma. Dosage Forms and Tech. 4 (2): pp. 74-79 (2011).
Nguyen, Tien, "Drug Structures Made Public in New Orleans," https://cen.acs.org/articles/96/web/2018/03/Drug-structures-made-public-New-Orleans.html; 5 pages (2018).
Oganov, et al. "The Importance of Evidence-Based Medicine for Clinical Practice. Fundamentals of Evidence-Based Medicine," Silicea-Polygraph, p. 11, paragraphs 2-3, with partial English translation, Moscow, 2010, 4 pages.
Owens, Timothy, "Discovery of PRN1008: A reversible covalent BTK inhibitor for treatment of autoimmune diseases," 255th ACS National Meeting & Exposition, New Orleans, LA, United States, 2 pages (2018).
Perricone et al., "Immune thrombocytopenia purpura (ITP) associated with vaccinations: a review of reported cases," Immunol Res. 60(2-3), 2014, pp. 226-235.
Rigg et al., "Oral administration of Bruton's tyrosine kinase inhibitors impairs GPVI-mediated platelet function", Am J Physiol Cell Physiol., 310(5), pp. C373-380 (2015).
Sergeev, P.V., "Short Course of Molecular Pharmacology," N. I. Pirogov Second Moscow Medical Institute, Moscow, 1975 with partial English translation, 3 pages.
Thakuria et al., "Crystal Polymorphism in Pharmaceutical Science," Comprehensive Supramolecular Chemistry II, vol. 5, pp. 283-309 (2017).

* cited by examiner

METHODS FOR TREATING DRUG AND VACCINE INDUCED IMMUNE THROMBOCYTOPENIA BY ADMINISTERING SPECIFIC COMPOUNDS

CROSS-REFERENCE TO RELATED APPLICATIONS

This application is a national phase entry pursuant to 35 U.S.C. § 371 of International Application No. PCT/US2022/024806, filed Apr. 14, 2022, which claims the benefit of priority to U.S. Provisional Application No. 63/175,976, filed Apr. 16, 2021, the entire contents of which are incorporated herein by reference for all purposes.

BACKGROUND AND SUMMARY

Drug-induced thrombocytopenia (DITP) and vaccine-induced thrombosis and thrombocytopenia (VITT) have a clinical resemblance to autoimmune heparin induced thrombocytopenia (HIT), with the majority of patients testing positive for anti-platelet factor 4 (PF4) antibodies. Greinacher et al., Thrombotic thrombocytopenia after ChAdox1 nCov-19 vaccination, N Engl J Med, doi:10.1056/NEJMoa2104840 (2021); Greinacher et al., Autoimmune heparin-induced thrombocytopenia, J Thromb Haemost 15(11): 2099-114 (2017). In HIT, IgG-containing immune complexes bind and cross-link the platelet surface receptor FcγRIIA (CD32a), a low affinity Fc receptor (FcR) that binds immune complexes with high avidity, and initiate platelet activation. Greinacher et al., Autoimmune heparin-induced thrombocytopenia, J Thromb Haemost 15(11):2099-114 (2017). Autoimmune HIT, despite the name, is rare but occurs independently of heparin and result in persistent severe thrombocytopenia together with DIC and microvascular thrombosis. Id.

Novel, safe, and effective oral treatments to maintain platelet counts in DITP and VITT patients would represent a significant therapeutic advantage over current standard of care. Accordingly, disclosed herein are novel methods for the treatment and/or prevention of DITP and VITT with specific compounds.

Bruton's agammaglobulinemia tyrosine kinase (BTK) is an essential signaling element downstream of the B-cell receptor (BCR), Fc-gamma receptor (FcγR), and Fc-epsilon receptor (FcR). BTK is a non-receptor tyrosine kinase and a member of the TEC family of kinases. BTK is essential to B cell lineage maturation, and inhibition of BTK activity in cells produces phenotypic changes consistent with blockade of the BCR. Illustratively, BTK inhibition results in the down-regulation of various B-cell activities, including cell proliferation, differentiation, maturation, and survival, and the up-regulation of apoptosis.

Rather than acting in an "on/off switch" manner, BTK may be best viewed as an immune function "modulator" (Crofford U et al., 2016; Pal Singh S et al., 2018). Important insights into BTK function come from loss of function analyses in humans and mice. Individuals with loss of function mutations in the BTK gene develop X-linked agammaglobulinemia (XLA), characterized by a complete absence of circulating B cells and plasma cells, and very low levels of immunoglobulins of all classes (Tsukada 1993, Vetrie 1993). This indicates the potential for BTK inhibition to suppress production of autoantibodies thought to be important in the development of autoimmune diseases.

While BTK is not expressed in T cells, natural killer cells, and plasma cells and has no traceable direct functions in T cells and plasma cells (Sideras and Smith 1995; Mohamed et al., 2009), the enzyme regulates the activation of other hematopoietic cells, such as basophils, mast cells, macrophages, neutrophils, and platelets. For example, BTK plays a role in the activation of neutrophils, which are key players in the inflammatory response that contributes to wound healing but may also cause tissue damage (Volmering S et al., 2016).

Accordingly, a selective BTK inhibitor has the potential to target multiple pathways involved in inflammation and autoimmunity, including, but not limited to: blocking BCR; inhibiting plasma cell differentiation and antibody production; blocking IgG-mediated FcγR activation, phagocytosis, and inflammatory mediators in monocytes or macrophages; blocking IgE-mediated FcεR activation and degranulation in mast cells or basophils; and inhibiting activation, adhesion, recruitment, and oxidative burst in neutrophils. Based on these effects, a selective BTK inhibitor may block the initiation and progression of various inflammatory diseases and mitigate tissue damage resulting from these diseases. Although individuals with loss of function mutations in the BTK gene have decreased humoral immunity and are susceptible to pyogenic bacterial and enterovirus infections, requiring treatment with intravenous immunoglobulin, inhibition of BTK in individuals with an intact immune system is not predicted to produce similar susceptibility to infection.

Several orally administered BTK inhibitors (BTKi), including ibrutinib (PCI-32765) and spebrutinib (CC-292), are currently marketed or in clinical development for a range of indications (Lee A et al., 2017). For example, ibrutinib has provided further clinical validation of the BTK target and was recently approved for human use in mantle cell lymphoma, Waldenström's macroglobulinemia, and chronic lymphocytic leukemia by the U.S. Food and Drug Administration (FDA) (Imbruvica Package Insert, 2015). Ibrutinib has also demonstrated activity in other hematological malignancies (Wang 2013 Byrd 2013),), and most recently for use as an antiplatelet agent (Nicolson P L et al. (2020) Haematologica 106(1):208-219; doi.org/10.3324/haematol.2019.218545) and for counteracting thrombocytopenia occurring shortly after vaccination with the COVID-19 vaccine AZD1222 (Vaxzevria) (von Hundelshausen et al. (2021) Thromb Haemost. April 13. Doi 10.1055/a-1481-3039). In addition, CC-292 has been reported to be well tolerated in a healthy volunteer population at doses which provide 100% occupancy of the BTK enzyme (Evans 2013). Furthermore, evobrutinib recently demonstrated efficacy for multiple sclerosis in a Phase 2 trial (Montalban X et al., 2019). Other BTKi compounds are in clinical development for various immune-mediated disorders, such as pemphigus (NCT02704429), rheumatoid arthritis (NCT03823378, NCT03682705, NCT03233230), and asthma (NCT03944707) (Montalban X et al., 2019; Norman P 2016; Tam C S et al., 2018; Crawford J J et al., 2018; Min T K et al., 2019; Gillooly K M 2017; Nadeem A et al., 2019).

Some BTK inhibitors can cause bleeding and therefore would not be ideal candidates for use in subjects who are thrombocytopenic, anticoagulated, and/or have intracerebral bleeding. Langrish C L et al. (2021) *J Immunol.* April 1; 206(7):1454-1468. PMID: 33674445; PMCID: PMC7980532. However, Compound (I) as disclosed has no impact on normal platelet function in vitro and has not been associated with bleeding in thrombocytopenic patients, and in fact is being investigated in treating immune thrombocytopenia (ITP).

Compound (I), also known as "rilzabrutinib," as described herein, is a BTK inhibitor of the following structure:

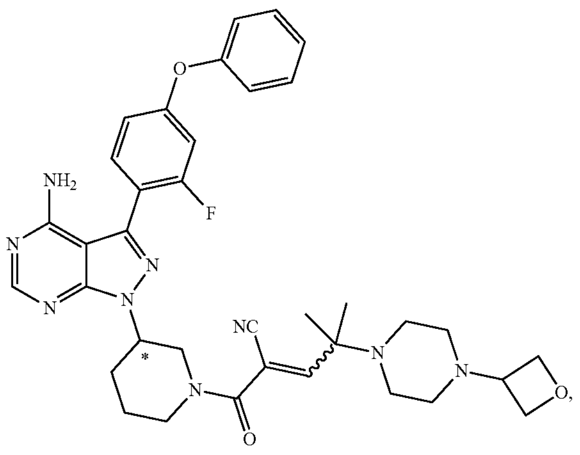 [SMILES: CC(C)(C=C(C#N)C(=O)N1CCCC(n2nc(-c3ccc(Oc4ccccc4)cc3F)c3c(N)ncnc32)C1)N1CCN(C2COC2)CC1]

wherein *C is a stereochemical center. See PCT Publication No. WO 2014/039899, which is incorporated herein by reference, e.g., Example 31.

This compound has been disclosed in several patent publications, such as, e.g., PCT Publication Nos. WO 2014/039899, WO 2015/127310, WO 2016/100914, WO 2016/105531, and WO 2018/005849, the contents of each of which are incorporated by reference herein.

Rilzabrutinib is a novel, highly selective, small molecule inhibitor of non-T cell white blood cell signaling via B-cell receptor, FCγR, and/or FcεR signaling of the BTK pathway. Rilzabrutinib functions as a reversible covalent BTK inhibitor and forms both a non-covalent and a covalent bond with its target, allowing for enhanced selectivity and extended inhibition with low systemic exposure. In comparison to first and second generation BTKi, rilzabrutinib has shown minimal cross-reactivity with other molecules and is low risk for off-target effects (Smith P F et al., 2017). Importantly, rilzabrutinib's reversible binding minimizes the likelihood of permanently modified peptides (Serafimova IM 2012). In addition, rilzabrutinib shows improved kinase selectivity relative to the covalent BTK inhibitor ibrutinib, with rilzabrutinib (1 μM) achieving >90% inhibition for 6 kinases compared to 21 kinases for ibrutinib (1 μM) in a 251-kinase panel.

Rilzabrutinib has shown encouraging results for the treatment of immune-mediated diseases. Rilzabrutinib is the most advanced BTKi in development for an autoimmune disease (Phase 3, NCT03762265) and the first BTKi to be evaluated in the treatment of pemphigus, a blistering disease that, like ITP, is autoantibody-driven. In humans, rilzabrutinib is rapidly absorbed following oral administration, with a fast half-life (3-4 h) and variable pharmacokinetics (PK).

Compound (II), also known as "atuzabrutinib," as described herein is a BTK inhibitor of the following structure:

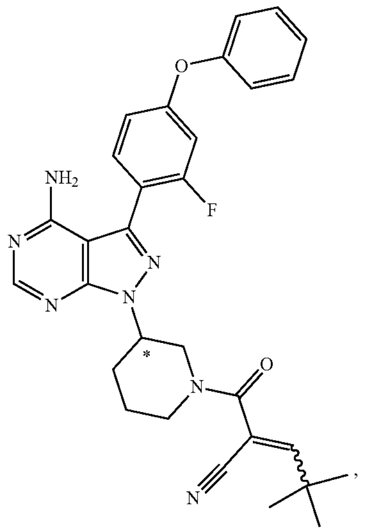 [SMILES: CC(C)(C)C=C(C#N)C(=O)N1CCCC(n2nc(-c3ccc(Oc4ccccc4)cc3F)c3c(N)ncnc32)C1]

where *C is a stereochemical center. This compound has been disclosed in e.g., WO 2012/158764 (see, e.g., Compound 125A/125B in Table 1), which is incorporated herein by reference.

In accordance herein, the following non-limiting embodiments are encompassed:

Embodiment 1. A method for treating or preventing drug-induced thrombocytopenia (DITP) in a human subject in need thereof comprising administering to the human subject a therapeutically effective amount of at least one BTK inhibitor selected from Compound (I), Compound (II), and pharmaceutically acceptable salts thereof.

Embodiment 2. A method for treating or preventing vaccine-induced thrombosis and thrombocytopenia syndrome (VITT) in a human subject in need thereof comprising administering to the human subject a therapeutically effective amount of at least one BTK inhibitor selected from Compound (I), Compound (II), and pharmaceutically acceptable salts thereof.

Embodiment 3. A method for increasing platelet count in a human subject with drug-induced thrombocytopenia (DITP) or vaccine-induced thrombosis and thrombocytopenia syndrome (VITT) comprising administering to the human subject a therapeutically effective amount of at least one BTK inhibitor selected from Compound (I), Compound (II), and pharmaceutically acceptable salts thereof.

Embodiment 4. A method for reducing platelet aggregation in a human subject with drug-induced thrombocytopenia (DITP) or vaccine-induced thrombosis and thrombocytopenia syndrome (VITT) comprising administering to the human subject a therapeutically effective amount of at least one BTK inhibitor selected from Compound (I), Compound (II), and pharmaceutically acceptable salts thereof.

Embodiment 5. The method of any one of embodiments 1-4, wherein, prior to administration, the human subject has at least one characteristic chosen from:

a. elevated D-dimer levels;

b. thrombosis; and c. anti-platelet factor 4 (PF4) antibodies.

Embodiment 6. The method of any one of embodiments 1, and 3-5, wherein the drug-induced thrombocytopenia (DITP) is induced by administration of a small molecule, protein, or components, diluents, excipients or the like found in therapeutic treatments.

Embodiment 7. The method of any one of embodiments 1, and 3-6, wherein the drug-induced thrombocytopenia (DITP) is induced by administration of unfractionated heparin, enoxaparin, dalteparin, tinzaparin, acenocoumarol, acetaminophen, acetyldigoxin, alfacalcidol, allopurinol, alteplase, amphotericin B, argatroban, aspirin, atenolol, azathioprine, bivalirudin, bortezomib, capecitabine, captopril, carbamazepine, carboplatin, carfilzomib, ceftriaxone, cephalexin, chlorthalidone, cilastin/imipenem, clopidogrel, clozapine, cyclocytidine, dactinomucin/actinomycin, deferasirox, deferiprone, diflunisal, digoxin, dipyridamole, drospirenone/ethinylestradiol, eltrombopag, epoetin alfa, eporestenol, eptifibatide, famotidine, fluconazole, fluorouracil, furosemide, fusidic acid, ganciclovir, gemcitabine, gentamicin, glycoprotein IIB/IIA inhibitor, gold, hydrochlorothiazide, hydrochlorothiazide/triamterene, hydroxychloroquine, imatinib, inamrinone, intergrilin, ITP drugs, ixazomib, lenalidomide, levetiracetam, linezolid, melperone, menatetrenone, meropenem, methotrexate, metoprolol, molsidomine, nedaplatin, nicotinamide, nitrofurantoin, nonsteroidal anti-inflammatory drugs (NSAIDS) (e.g., ibuprofen, naproxen, celecoxib, diclofenac, and the like), octreotide, pantroprazole, penicillamine, phenytoin, piperacillin, propranolol, proton pump inhibitors, quinine, rifampin, ruxolitinib, ruxolitnib phosphate, sirolimus, spironolactone, streptokinase, sulfamethoxazole, sulfisoxazole, sunitinib, teicoplanin, temozolomide, temsirolimus, ticlopidine, tirofiban, trimethoprim/sulfamethoxazole, urokinase, valganciclovir, valproic acid, vancomycin, warfarin, or combinations thereof.

Embodiment 8. The method of any one of embodiments 1, and 3-6, wherein the drug-induced thrombocytopenia (DITP) is induced by administration of filgrastim (granulocyte colony stimulating factor; G-CSF), interferon, interferon alpha, peginterferon alfa 2B, peginterferon alfa 2B/ribavirin, factor VIII, TNF alpha, INF gamma, or combinations thereof.

Embodiment 9. The method of any one of embodiments 1, and 3-6, wherein the drug-induced thrombocytopenia (DITP) is induced by administration of abciximab, adalimumab, alemtuzumab, antibody-drug conjugates, anti-thymocyte globulin, brentuximab, cixutumumab, efaluzumab, natalizumab, rituximab, trastuzumab, or combinations thereof.

Embodiment 10. The method of any one of embodiments 2-5, wherein the vaccine-induced thrombosis and thrombocytopenia syndrome (VITT) is induced by administration of a vaccine.

Embodiment 11. The method of any one of embodiments 2-5, and 10, wherein the vaccine-induced thrombosis and thrombocytopenia syndrome (VITT) is induced by administration of a vaccine delivered in an adenoviral vector.

Embodiment 12. The method of embodiment 11, wherein the adenoviral vector comprises a therapeutic and/or prophylactic agent.

Embodiment 13. The method of embodiment 12, wherein the therapeutic or prophylactic agent is a gene therapy.

Embodiment 14. The method of any one of embodiments 10-13, wherein the vaccine is to prevent a coronavirus infection.

Embodiment 15. The method of embodiment 14, wherein the coronavirus infection is COVID-19.

Embodiment 16. The method of any one of embodiments 10-13, wherein the vaccine is to prevent an infection selected from measles, mumps, rubella, varicella, herpes simplex virus 1, herpes simplex virus 2, varicella, rotavirus, influenza, yellow fever, smallpox, hepatitis B, human papilloma virus, pneumococcus, hepatitis A, anthrax, diphtheria, acellular pertussis, hemophilus influenzae, including type B, meningococcus C, meningitis, typhoid, rabies, Lyme disease, tetanus, or any combination thereof.

Embodiment 17. The method of any one embodiments 1-16, wherein Compound I is (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, a mixture of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and (S)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or an individual (E)- or (Z)-isomer of any of the above compounds; and/or a pharmaceutically acceptable salt of any of the above compounds.

Embodiment 18. The method of embodiment 17, wherein Compound I is the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof.

Embodiment 19. The method of embodiment 17, wherein Compound I is the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof.

Embodiment 20. The method of embodiment 17, wherein Compound I is a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof.

Embodiment 21. The method of any one of embodiments 1-17, wherein Compound II is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, a mixture of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, or an individual (E)- or (Z)-isomer of any of the above compounds; and/or a pharmaceutically acceptable salt of any of the above compounds.

Embodiment 22. The method of embodiment 21, wherein Compound II is the (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof.

Embodiment 23. The method of embodiment 21, wherein Compound II is the (Z) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof.

Embodiment 24. The method of embodiment 21, wherein Compound II is a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof.

Additional objects and advantages will be set forth in part in the description which follows, and in part will be understood from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 1A shows representative aggregation traces. FIGS. 1B and 1C depict the quantification of maximum aggregation through area under the curve (AUC), as measured for 10 minutes for P2, P3, P4, and P7 pre- and post-IVIg samples (FIG. 1B), and P1, P5, and P6 post-IVIg (FIG. 1C) and plasma exchange samples. Mean±SEM, n=3. Statistical analysis was by two-way ANOVA with Dunnett multiple comparisons, * $p<0.05$, ns: non-significant.

FIG. 2A shows representative aggregation traces. FIG. 2B shows quantification of maximum aggregation. Statistical analysis was by one-way ANOVA with Dunnett multiple comparisons. Mean±SEM, n=7·*$p<0.05$.

DETAILED DESCRIPTION

Definitions

Figure 1A:
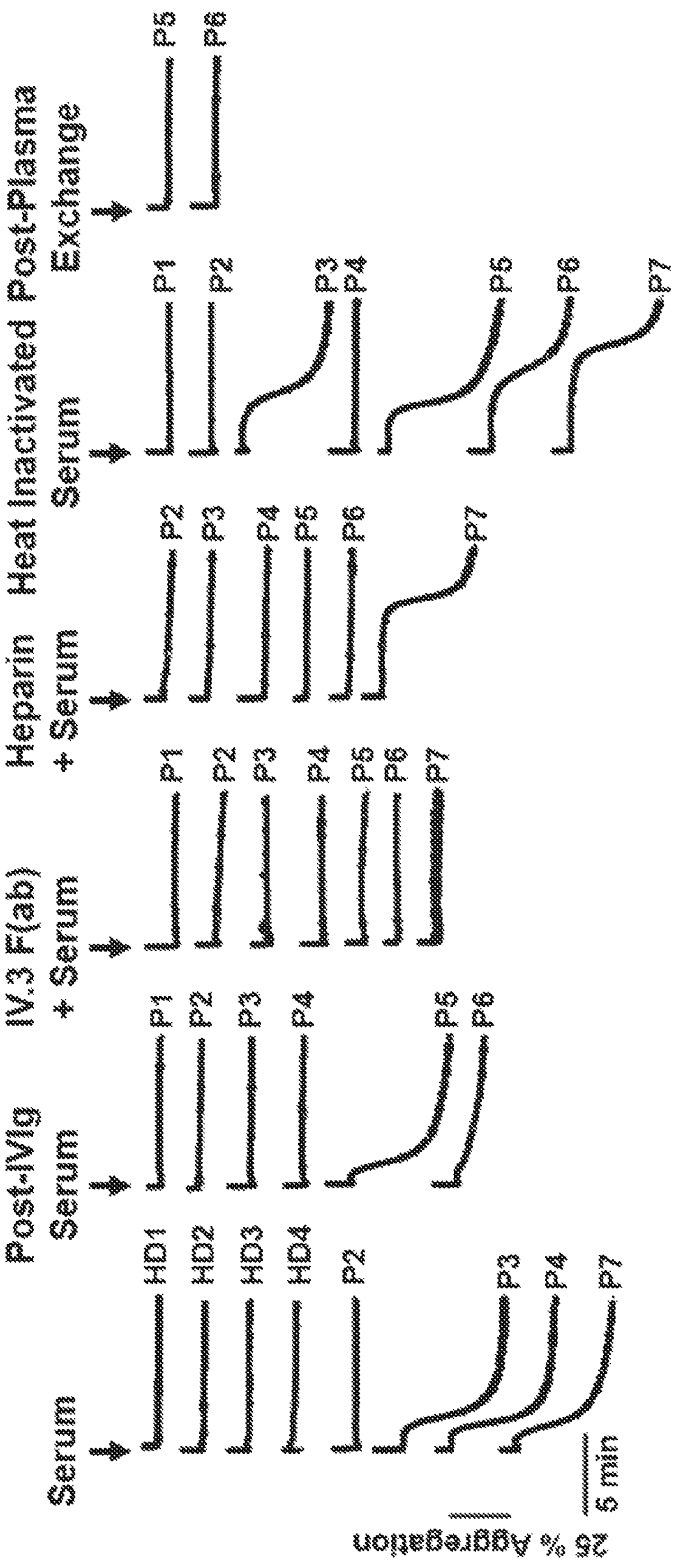
FIGS. 1A-1C show serum from patients with vaccine-induced thrombosis and thrombocytopenia syndrome (VITT) induces platelet aggregation via the FcγRIIA. Washed platelets ($2\times10^8$/mL) were stimulated with serum (1:15, v/v) from healthy donors (HD) or patient with VITT (P) pre- and post-intravenous immunoglobulin (IVIg) treatment or in the presence of 10 μg/mL IV.3 F(ab), low concentration heparin (0.2 U/mL), or following heat inactivation (56° C., 45 minutes). Platelet aggregation was measured for each condition.

Unless otherwise stated, the following terms used in the specification and claims are defined for the purposes of this Application and have the following meanings. All undefined technical and scientific terms used in this Application have the meaning as commonly understood by one of ordinary skill in the art to which this disclosure belongs.

As used herein, "a" or "an" entity refers to one or more of that entity; for example, a compound refers to one or more compounds or at least one compound unless stated otherwise. As such, the terms "a" (or "an"), "one or more", and "at least one" can be used interchangeably herein.

As used herein, the term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. With regard to specific values, it should be understood that specific values described herein for subject populations (e.g., the subject of the described clinical trial) represent median, mean, or statistical numbers, unless otherwise provided. Accordingly, aspects of the present disclosure requiring a particular value in a subject are supported herein by population data in which the relevant value is assessed to be a meaningful delimitation on the subject population.

As used herein, the term "active pharmaceutical ingredient" or "therapeutic agent" ("API") refers to a biologically active compound.

As used herein, the terms "administer," "administering," or "administration" herein refer to providing, giving, dosing, and/or prescribing by either a health practitioner or an authorized agent and/or putting into, taking or consuming by the patient or person himself or herself. For example, "administration" of an API to a patient refers to any route (e.g., oral delivery) of introducing or delivering the API to the patient. Administration includes self-administration and administration by another.

As used herein, "immune thrombocytopenia" (ITP) encompasses or at least also refers to other terms commonly used such as idiopathic thrombocytopenia and idiopathic thrombocytopenic purpura. There are two main types of ITP: short (acute) and chronic (long term). Acute ITP typically lasts less than six months, whereas chronic ITP can last six months or longer. ITP affects multiple age groups and can be seen in children, teenagers, and adults.

ITP is a disorder that can lead to easy or excessive bruising and bleeding. The bleeding results from unusually low levels of platelets. ITP may result from the development of an antibody directed against a structural platelet antigen. In childhood ITP, the antibody may be triggered by viral antigens. In adults, the trigger is unknown, although ITP has been associated with *Helicobacter pylori* infections, and treatment of the infections has been followed by remission of the ITP. ITP may worsen during pregnancy and may increase the risk of maternal morbidity. In some embodiments, ITP may be induced by a drug (i.e., drug-induced immune thrombocytopenia; DITP), such as a small molecule or an antibody.

As used herein, "drug-induced immune thrombocytopenia" (DITP) refers to acute, immune-mediated thrombocytopenia, which may be suspected when a subject has sudden, severe thrombocytopenia. DITP is induced by a drug. Exemplary and non-limiting drugs that can induce DITP include small molecules, proteins, antibodies, as well as compositions and/or compounds used in therapeutic treatments.

As used herein, "vaccine-induced immune thrombosis and thrombocytopenia" (VITT) refers to blood clotting with low levels of platelets (i.e., thrombosis with thrombocytopenia), disseminated intravascular coagulation (DIC) and bleeding with high mortality that is induced by a vaccine. In some embodiments, VITT is induced by a COVID-19 vaccine. COVID-19 vaccines may comprise whole virus, attenuated virus, viral particle, protein, nucleic acid, and/or viral vector. In some embodiments, the COVID-19 vaccine is a viral vector vaccine. In some embodiments, the COVID-19 vaccine is an adenoviral vector vaccine. In some embodiments, the vaccine is AZD1222 (Oxford-AstraZeneca; formerly ChAdox1 nCoV-19). VITT may sometimes be called "vaccine-induced prothrombotic immune thrombocytopenia (VIPIT)," and both are encompassed herein (i.e., VITT includes VITT and VIPIT).

As used herein, a "pharmaceutically acceptable carrier or excipient" means a carrier or an excipient that is useful in preparing a pharmaceutical composition that is generally safe, and neither biologically nor otherwise undesirable, such as, e.g., a carrier or an excipient that is acceptable for mammalian pharmaceutical use.

As used herein, the term "pharmaceutically acceptable salt" refers to a salt form, e.g., an acid addition salt, of an active pharmaceutical agent that is pharmaceutically acceptable and that possesses the desired pharmacological activity of the API of which the salt is made. Pharmaceutically acceptable salts are well known in the art and include those derived from suitable inorganic and organic acids. Such salts include, but are not limited to, salts formed with inorganic acids such as hydrochloric acid, hydrobromic acid, sulfuric acid, phosphoric acid, and the like; or formed with organic acids such as formic acid, acetic acid, propionic acid, hexanoic acid, lactic acid, malonic acid, succinic acid, malic acid, maleic acid, fumaric acid, tartaric acid, citric acid, benzoic acid, mandelic acid, methanesulfonic acid, ethanesulfonic acid, 1,2-ethanedisulfonic acid, benzenesulfonic acid, 4-toluenesulfonic acid, and the like. S. M. Berge et al. describes pharmaceutically acceptable salts in detail in J. Pharmaceutical Sciences, 1977, 66, 1-19.

As used herein, the terms "Compound (I)," "rilzabrutinib," "(R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile" and "2-[(3R)-3-[4-amino-3-(2-fluoro-4-phenoxy-phenyl)pyrazolo[3,4-d]-pyrimidin-1-yl]piperidine-1-carbonyl]-4-methyl-4-[4-(oxetan-3-yl)piperazin-1-yl]pent-2-enenitrile" are used interchangeably to refer to a compound having the structure:

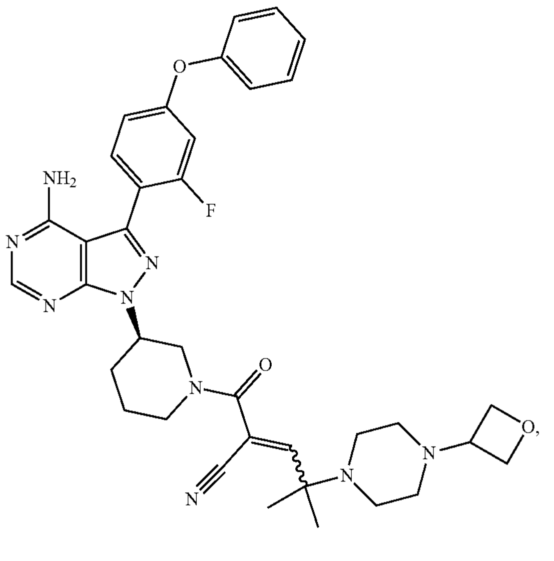 [SMILES: CC(C)(C=C(C#N)C(=O)N1CCC[C@@H](n2nc(-c3ccc(Oc4ccccc4)cc3F)c3c(N)ncnc32)C1)N1CCN(C2COC2)CC1]

where *C is a stereochemical center.

A dose of rilzabrutinib may contain the corresponding (S) enantiomer as an impurity in less than about 5% by weight, such as, e.g., as an impurity in less than about 1% by weight. Similarly, a dose of the (E) isomer of rilzabrutinib may contain the corresponding (Z) isomer as an impurity in less than about 1% by weight; a dose of the (Z) isomer of rilzabrutinib may contain the corresponding (E) isomer as an impurity in less than about 1% by weight. When rilzabrutinib is denoted as a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, it means that the amount of (E) or (Z) isomer in the mixture is greater than about 1% by weight. In some embodiments, the molar ratio of (E) to (Z) isomer is 9:1.

As used herein, "Compound (II)" and "atuzabrutinib," are used interchangeably to refer to the (E) isomer, (Z) isomer, or a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, or a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, which has the following structure:

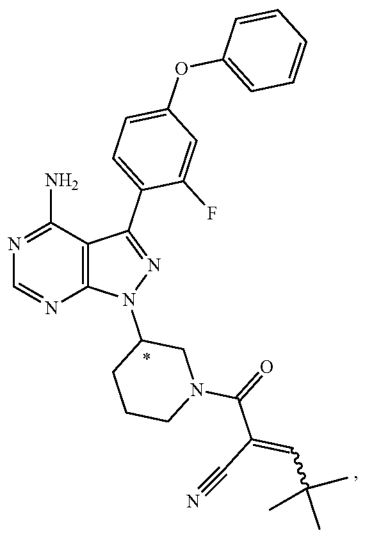 [SMILES: CC(C)(C)C=C(C#N)C(=O)N1CCCC(n2nc(-c3ccc(Oc4ccccc4)cc3F)c3c(N)ncnc32)C1]

where *C is a stereochemical center.

When Compound (II) is denoted as (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, it may also contain the corresponding (S) enantiomer as an impurity in less than 5% by weight, such as, e.g., an impurity in less than 1% by weight. Accordingly, when the Compound (II) is denoted as a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, the amount of (R) or (S) enantiomer in the mixture is greater than 1% by weight. Similarly, when Compound (II) is denoted as the (E) isomer, it may contain the corresponding (Z) isomer as an impurity in less than 5% by weight, such as less than 1% by weight. Accordingly, when the Compound (II) is denoted as a mixture of (E) and (Z) isomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, the amount of (E) or (Z) isomer in the mixture is greater than 1% by weight.

In some embodiments, Compound (II) is a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, Compound (II) is substantially (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (II) is at least about 75%, e.g., at least about 80%, at least about 85%, at least about 90%, at least about 95%, by weight (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (II) is at least about 95% by weight (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

As used herein, the term "therapeutically effective amount" refers to that an of a compound that produces the desired effect for which it is administered (e.g., improvement in DITP or a symptom of DITP, or lessening the severity of DITP or a symptom of DITP, or improvement in VITT or a symptom of VITT, or lessening the severity of VITT or a symptom of VITT). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the term "treat," "treating," or "treatment," when used in connection with a disorder or condition, includes any effect, e.g., lessening, reducing, modulating, ameliorating, or eliminating, that results in the improvement of the disorder or condition. Improvements in or lessening the severity of any symptom of the disorder or condition can be readily assessed according to standard methods and techniques known in the art.

"Preventing," as used herein, includes providing prophylaxis with respect to the occurrence or recurrence of a disease, disorder, or condition in a subject that may be predisposed to the disease, disorder, or condition but has not yet been diagnosed with the disease, disorder, or condition. Unless otherwise specified, the terms "prevent," "prevention," "reduce," "inhibit," or "prevent" do not denote or require complete prevention over all time.

In accordance with the description, provided herein is a method for treating or preventing drug-induced thrombocytopenia (DITP) in a human subject in need thereof comprising administering to the human subject a therapeutically effective amount of at least one BTK inhibitor selected from Compound (I):

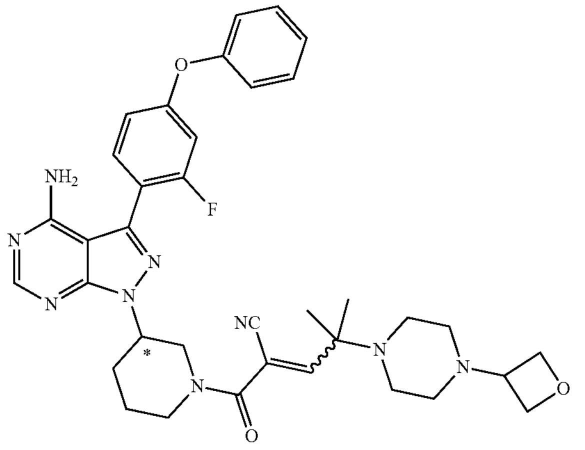 [SMILES: CC(C)(C=C(C#N)C(=O)N1CCCC(n2nc(-c3ccc(Oc4ccccc4)cc3F)c3c(N)ncnc32)C1)N1CCN(C2COC2)CC1]

where *C is a stereochemical center,

Compound (II):

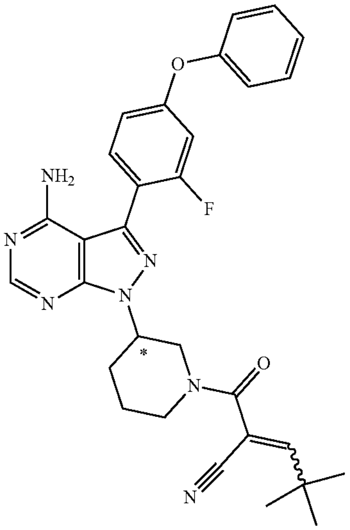 [SMILES: CC(C)(C)C=C(C#N)C(=O)N1CCCC(n2nc(-c3ccc(Oc4ccccc4)cc3F)c3c(N)ncnc32)C1]

where *C is a stereochemical center, and pharmaceutically acceptable salts thereof.

Also provided herein is a method for treating or preventing vaccine-induced thrombosis and thrombocytopenia syndrome (VITT) in a human subject in need thereof comprising administering to the human subject a therapeutically effective amount of at least one BTK inhibitor selected from Compound (I), Compound (II), and pharmaceutically acceptable salts thereof.

In some embodiments, a method for increasing platelet count in a human subject with drug-induced thrombocytopenia (DITP) or vaccine-induced thrombosis and thrombocytopenia syndrome (VITT) comprising administering to the human subject a therapeutically effective amount of at least one BTK inhibitor selected from Compound (I), Compound (II), and pharmaceutically acceptable salts thereof.

In some embodiments, a method for reducing platelet aggregation in a human subject with drug-induced thrombocytopenia (DITP) or vaccine-induced thrombosis and thrombocytopenia syndrome (VITT) comprising administering to the human subject a therapeutically effective amount of at least one BTK inhibitor selected from Compound (I), Compound (II), and pharmaceutically acceptable salts thereof.

In each instance, in some embodiments, prior to administration, the human subject has at least one characteristic chosen from: elevated D-dimer levels, thrombosis; and anti-platelet factor 4 (PF4) antibodies.

In embodiments related to drug-induced thrombocytopenia (DITP), the DITP may be induced by administration of a small molecule, protein, or components, diluents, excipients or the like found in therapeutic treatments.

In some embodiments, the drug-induced thrombocytopenia (DITP) is induced by administration of unfractionated heparin, enoxaparin, dalteparin, tinzaparin, acenocoumarol, acetaminophen, acetyldigoxin, alfacalcidol, allopurinol, alteplase, amphotericin B, argatroban, aspirin, atenolol, azathioprine, bivalirudin, bortezomib, capecitabine, captopril, carbamazepine, carboplatin, carfilzomib, ceftriaxone, cephalexin, chlorthalidone, cilastin/imipenem, clopidogrel, clozapine, cyclocytidine, dactinomucin/actinomycin, deferasirox, deferiprone, diflunisal, digoxin, dipyridamole, drospirenone/ethinylestradiol, eltrombopag, epoetin alfa, eporestenol, eptifibatide, famotidine, fluconazole, fluorouracil, furosemide, fusidic acid, ganciclovir, gemcitabine, gentamicin, glycoprotein JIB/IIA inhibitor, gold, hydrochlorothiazide, hydrochlorothiazide/triamterene, hydroxychloroquine, imatinib, inamrinone, intergrilin, ITP drugs, ixazomib, lenalidomide, levetiracetam, linezolid, melperone, menatetrenone, meropenem, methotrexate, metoprolol, molsidomine, nedaplatin, nicotinamide, nitrofurantoin, nonsteroidal anti-inflammatory drugs (NSAIDS) (e.g., ibuprofen, naproxen, celecoxib, diclofenac, and the like), octreotide, pantroprazole, penicillamine, phenytoin, piperacillin, propranolol, proton pump inhibitors, quinine, rifampin, ruxolitinib, ruxolitnib phosphate, sirolimus, spironolactone, streptokinase, sulfamethoxazole, sulfisoxazole, sunitinib, teicoplanin, temozolomide, temsirolimus, ticlopidine, tirofiban, trimethoprim/sulfamethoxazole, urokinase, valganciclovir, valproic acid, vancomycin, warfarin, or combinations thereof.

In some embodiments, the drug-induced thrombocytopenia (DITP) is induced by administration of filgrastim (granulocyte colony stimulating factor; G-CSF), interferon, interferon alpha, peginterferon alfa 2B, peginterferon alfa 2B/ribavirin, factor VIII, TNF alpha, INF gamma, or combinations thereof.

In some embodiments, the drug-induced thrombocytopenia (DITP) is induced by administration of abciximab, adalimumab, alemtuzumab, antibody-drug conjugates, antithymocyte globulin, brentuximab, cixutumumab, efaluzumab, natalizumab, rituximab, trastuzumab, or combinations thereof.

In embodiments relating to vaccine-induced thrombosis and thrombocytopenia syndrome (VITT), the VITT may be induced by administration of a vaccine. In some embodiments, the (VITT) is induced by administration of a vaccine delivered in an adenoviral vector. In certain aspects, the adenoviral vector comprises a therapeutic and/or prophylactic agent. In some embodiments, the therapeutic or prophylactic agent is a gene therapy. In some embodiments, the vaccine is to prevent a coronavirus infection. In some embodiments, the coronavirus infection is COVID-19. In some embodiments, the vaccine is AZD1222 (Oxford-AstraZeneca COVID-19 vaccine).

In some embodiments, the vaccine is to prevent an infection selected from measles, mumps, rubella, varicella, herpes simplex virus 1, herpes simplex virus 2, varicella, rotavirus, influenza, yellow fever, smallpox, hepatitis B, human papilloma virus, pneumococcus, hepatitis A, anthrax, diphtheria, acellular pertussis, hemophilus influenzae, including type B, meningococcus C, meningitis, typhoid, rabies, Lyme disease, tetanus, or any combination thereof.

In some embodiments, Compound I is (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, a mixture of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and (S)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or an individual (E)- or (Z)-isomer of any of the above compounds; and/or a pharmaceutically acceptable salt of any of the above compounds.

In some embodiments, Compound I is the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof.

In some embodiments, Compound I is the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof.

In some embodiments, Compound I is a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof.

In some embodiments, Compound II is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, a mixture of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, or an individual (E)- or (Z)-isomer of any of the above compounds; and/or a pharmaceutically acceptable salt of any of the above compounds.

In some embodiments, Compound II is the (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof.

In some embodiments, Compound II is the (Z) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof.

In some embodiments, Compound II is a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof.

EXAMPLES

Example 1. Methods

A. Subjects

Patients presenting with thrombosis and thrombocytopenia, occurring after vaccination with the AstraZeneca vaccine AZD1222 (formerly ChAdox1 nCoV-19), were recruited.

B. Antibodies and Reagents

Mouse monoclonal IgG2b antibody against human CD32 (IV.3) was purified from hybridoma cells supernatant, and IV.3 F(ab) fragment was made using Pierce Fab Preparation kit (Thermo Fisher Scientific, Catalog #44985).

Serum Preparation: Patient and healthy donor serum was collected following centrifugation (2000×g, 10 minutes, room temperature (RT)) of clotted whole blood. Patient sera was collected before and after treatment with dexamethasone and intravenous immunoglobulin (IVIg; see Table 1 in Example 2).

C. Human Platelet Preparation

Washed platelets were prepared from citrated whole blood as described in Nicolson et al., Low-dose BTK inhibitors selectively block platelet activation by CLEC-2, Haematologica 106(1):208-19 (2021). Briefly; citrated blood was taken from healthy, drug-free volunteers and mixed (1:10, v/v) with acid citrate dextrose and centrifuged (200×g, 20 minutes, RT) to produce platelet rich plasma. Platelet rich plasma was then centrifuged (1000×g, 10 minutes, RT) in the presence of 0.2 μg/mL prostacyclin. The platelet pellet was resuspended in modified-Tyrode's-HEPES buffer, prepared as described in Nicolson et al., acid citrate dextrose and 0.2 μg/mL prostacyclin and centrifuged (1000×g, 10 minutes, RT). Platelet pellet was resuspended in modified-Tyrode's-HEPES buffer to a concentration of $2\times10^8$/mL and allowed to rest for 30 minutes prior to use.

D. Light Transmission Aggregometry (LTA)

Aggregation was measured in washed platelets ($2\times10^8$/mL) under stirring conditions (1200 rpm) at 37° C. using a light transmission aggregometer (Model 700, ChronoLog) for 20 minutes following stimulation with serum (1:15, v/v). Washed platelets were pre-incubated with IV.3 F(ab) for 5 minutes or with inhibitors for 10 minutes prior to stimulation with serum. Modified-Tyrode's-HEPES buffer or dimethyl sulfoxide (DMSO) was used as vehicle.

E. Statistical Analysis

All data are presented as mean±standard error of the mean (SEM), $p<0.05$ was considered statistically significant. Statistical analysis was performed in GraphPad Prism 9 (GraphPad Software Inc.) using one or two-way ANOVA with Dunnett corrections for multiple comparisons.

Example 2. Results

A. Patients with Vaccine-Induced Thrombosis and Thrombocytopenia Syndrome (VITT) Demonstrate Thrombosis, Thrombocytopenia, Elevated D-Dimer Levels and Anti-Platelet Factor 4 (PF4) Antibodies The presentation, investigation results, treatment and outcomes of seven patients with VITT are summarized in Table 1.

TABLE 1

Summary of patients with VITT.

| | Patient 1 | Patient 2 | Patient 3 | Patient 4 | Patient 5 | Patient 6 | Patient 7 |
|---|---|---|---|---|---|---|---|
| Age | 48 | 32 | 21 | 46 | 43 | 44 | 42 |
| Sex | Male | Female | Male | Female | Female | Male | Male |
| Platelet count at presentation ($\times10^9$/L) normal range 150-450 | 16 | 98 | 113 | 7 | 11 | 35 | 21 |
| D dimer (ng/ml) normal range 0-250 | 62342 | 6574 | 22903 | 31301 | 30324 | 6807 | 27000 |
| Fibrinogen (g/L) normal range 1.5-4 | 1.2 | <0.35 | 0.98 | 1.1 | 1.01 | <0.35 | 2.36 |
| Prothrombin Time Ratio normal range 0.8-1.2 | 1.2 | 1.5 | 1.3 | 1.2 | 1.1 | 1.4 | 1.1 |
| Activated Partial Thromboplastin Time Ratio normal range 0.8-1.2 | 1 | 1.7 | 0.8 | 1.1 | 1.2 | 1.6 | 1.3 |
| HIT Antibody Screen (Optical density) normal range 0.01-0.4 | 2.45 | 2.17 | 2.8 | >3.0 | 1.77 | 2.6 | >3.0 |
| Heparin-induced platelet activation (HITAlert) at presentation | | | | | | | |
| Platelet activation with serum normal range ≤ 8% | 24.79% | 31.2% | 55% | N/A | N/A | N/A | 75.31% |
| Platelet activation with serum and heparin normal range ≤ 8% | 18.53% | 18% | 36.5% | N/A | N/A | N/A | 22.63% |
| Platelet activation with serum and excess heparin normal range ≤ 8% | 0.64% | 3.68% | 1.43% | N/A | N/A | N/A | 4.38% |
| Clinical | CVST | CVST | Ischaemic stroke | CVST | CVST | CVST | CVST |
| Number of days post vaccine at presentation | 14 | 12 | 10 | 14 | 11 | 9 | 12 |

TABLE 1-continued

Summary of patients with VITT.

| | Patient 1 | Patient 2 | Patient 3 | Patient 4 | Patient 5 | Patient 6 | Patient 7 |
|---|---|---|---|---|---|---|---|
| Presentation symptoms | Headaches; Haematuria; Petechial rash; Subsequent development of left sided weakness | Occipital headache | Headache for 2-3 days; Collapse; Expressive dysphasia; | Headache | Headache, aura, petechial rash | Headache and vomiting for a few hours, followed by reduced conscious level | Headache for 1 wk, development of rightside weakness; subsequent seizure and collapse |
| Co-morbidities | Prostatitis | None | None | Hypothyroidism; Fibromyalgia Anxiety | None | None | None |
| Medications | None | None | None | Levothyroxine; Sertraline; Amitriptyline | None | None | None |
| Imaging findings at presentation | CVST Subarachnoid haemorrhage | CVST Subarachnoid haemorrhage intraparenchymal haemorrhage | Acute left ICA thrombus with multiple left middle MCA territory infarctions | CVST intraparenchymal haemorrhage | CVST | CVST; left-side intracerebral hemorrhage; midline shift | CVST; subarachnoid and intraparenchymal hemorrhage; globalized brain atrophy |
| Immunosuppression regime used | IVIg 0.5 g/kg OD for 2 consecutive days Dexamethasone 20 mg OD for 3 days | IVIg 1 g/kg for 2 consecutive days Dexamethasone 40 mg OD for 4 days | IVIg 1 g/kg single dose Dexamethasone 40 mg OD for 4 days | IVIg 1 g/kg single dose Dexamethasone 40 mg OD for 4 days. | IVIg 1 g/kg on 2 nonconsecutive days; dexamethasone 40 mg OD for 3 d | IVIg 1 g/kg on 2 nonconsecutive days dexamethasone 40 mg OD for 4 d | IVIg 1 g/kg single dose; dexamethasone 40 mg (2 doses) |
| Anticoagulant/ Antiplatelet regime used | Argatroban Fondaparinux 7.5 mg SC OD (when platelets normalized) | Argatroban | Fondaparinux 7.5 mg OD Apixaban 5 mg BD (on discharge) | Fondaparinux 2.5 mg SC OD (whilst platelets <50 × $10^9$/L) Fondaparinux 7.5 mg SC OD (when platelets ≥50 × $10^9$/L) Dabigatran 150 mg BD (on discharge) | Fondaparinux 7.5 mg SC OD | Argatroban Fondaparinux 7.5 mg SC OD (when platelets $050 3109/ L) | None |
| Other Treatments Required | Intubation | Intubation, thrombectomy | Thrombectomy | None | Plasma exchange | Intubation, thrombectomy, decompressive craniotomy, plasma exchange, platelet transfusion | Intubation, mannitol |
| Timing of first serum sample | Post-IVIg and Dexamethasone | Post-single dose of Dexamethasone | Pre-treatment | Pre-treatment | After IVIg and dexamethasone | After IVIg and dexamethasone | Pre-treatment |
| Timing of second serum sample | N/A | Post -IVIg and Dexamethasone | Post-IVIg and Dexamethasone | Post-IVIg and Dexamethasone | Post-PEX | Post-PEX | N/A |
| Days post IVIg that platelet count rose >50 x109/L | N/A - Nadir 59 × $10^9$/L (platelets 100 × $10^9$/L 48 hours after first IVIg infusion) | 2 days | N/A - nadir 52 × $10^9$/L (Platelets 198 × $10^9$/L three days after IVIg infusion) | 3 days | 4 days | 1 day | N/A; died < 24 h after IVIg |
| Outcome | Clinically recovered at time of discharge from hospital after 26 day admission | Death (support withdrawn following confirmation of brainstem death) | Clinically recovered at time of discharge from hospital after a 10 day admission; | Clinically recovered at time of discharge from hospital after a 16 day admission; 2 further admissions | Clinically recovered at time of discharge from hospital after a 12-d admission. | 36-d intensive care admission; ventilator-associated pneumonia; Limited neurological | Death 24 h after admission (rapid development of global ischemia before thrombectomy |

TABLE 1-continued

| Summary of patients with VITT. | | | | | | | |
|---|---|---|---|---|---|---|---|
| | Patient 1 | Patient 2 | Patient 3 | Patient 4 | Patient 5 | Patient 6 | Patient 7 |
| | | | ongoing mild right hand weakness and expressive dysphasia. | with headaches and drops in platelet counts; no further CVST; treated with (1st admission) prednisolone then (2nd admission) IVIg and rituximab; Remains in hospital. | | recovery; remains in hospital. | could be performed). |

BD, twice daily;
Continuous positive airway pressure, CPAP;
CVST, Cerebral venous sinus thrombosis;
ICA, Internal carotid artery;
IVIg, intravenous immunoglobulin;
MCA, Middle cerebral artery;
OD, once daily;
SC, Subcutaneous All seven patients were Caucasian, under the age of 50, and had not previously had symptomatic COVID-19. Patients presented with thrombosis (6 patients with cerebral venous sinus thrombosis [CVST] and 1 patient with ischemic stroke) and thrombocytopenia 9 to 14 days after the first AZD1222 vaccination. All patients presented with headaches, and one also had expressive dysphasia, 10-14 days following dosing with AZD1222. At presentation, clinical investigation revealed that all patients were thrombocytopenic (range: 7-113×$10^9$ platelets/L), with massively elevated D-dimer and low fibrinogen levels. Four patients were male, and three patients were female.

Despite no prior exposure to heparin, heparin-induced thrombocytopenia (HIT) screening with the anti-platelet factor 4 (PF4) IgG assay (Immucor catalog #HAT45G) showed strong reactivity in all patients. Using a Heparin Induced Platelet Activation (HIPA) assay (HITAlert™ kit; IQProducts Catalog IQP-396), sera in four of the patients tested showed platelet activation compared to patient serum that was reduced by low, and blocked by high, concentrations of heparin. These results are similar to reports of other patients with VITT. See, e.g., Greinacher et al., Thrombotic thrombocytopenia after ChAdOx1 nCov-19 vaccination, N Engl J Med, doi:10.1056/NEJMoa2104840 (2021); Schlutz et al., Thrombosis and thrombocytopenia after ChAdox1 nCoV-19 vaccination, N Engl J Med, doi:10.1056/NEJMoa2104882 (2021). Cross-sectional brain imaging verified the presence of cerebral venous sinus thrombosis (CVST) and intracerebral haemorrhage in three patients, and ischemic stroke caused by internal carotid artery thrombus in one patient.

All patients received intravenous immunoglobulin (IVIg) and the steroid dexamethasone, which is recommended by the British Society of Haematology guidelines for VITT (British Society for Haematology, Guidance produced from the expert haematology panel (EHP) focused on Covid-19 vaccine induced thrombosis and thrombocytopenia (VITT), b-s-h.org.uk/media/19530/guidance-version-13-on-mngmt-of-thrombosis-with-thrombocytopenia-occurring-after-c-19-vaccine_20210407.pdf (2021). Platelet counts improved over 1 to 4 days in all patients except one, who died 24 hours after presentation. At the time of writing, three patients had recovered and been discharged from the hospital with ongoing normal platelet counts, one patient remained in hospital, and two patients had died because of the sequelae of CVST and secondary intracerebral hemorrhage. One discharged patient who was taking dabigatran, relapsed with thrombocytopenia and headaches but without thrombosis or raised D-dimer, 8 weeks after discharge and required repeat treatment with IVIg and corticosteroids. Two patients received plasma exchange. Of note, IVIg has also been shown to rapidly inhibit HIT antibody induced platelet activation. Warkentin, High-dose intravenous immunoglobulin for the treatment and prevention of heparin-induced thrombocytopenia: a review, Expert Rev Hematol 12(8):685-98, doi: 10.1080/17474086.2019.1636645 (2019). Patients also received non-heparin anticoagulation, and two patients required intensive care unit support.

B. Serum from Patients with VITT Induces Platelet Aggregation

Figure 1B:
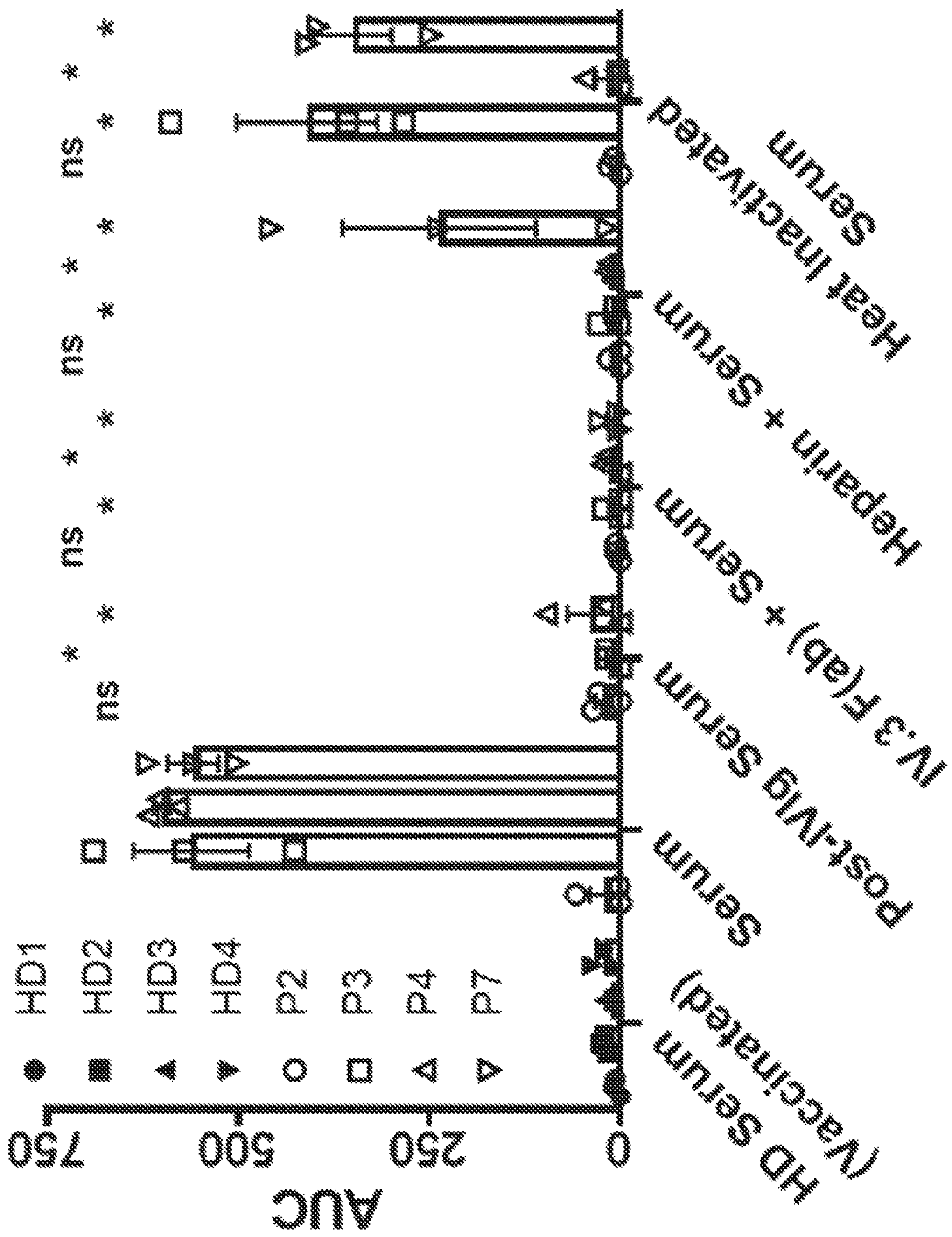
Figure 1C:
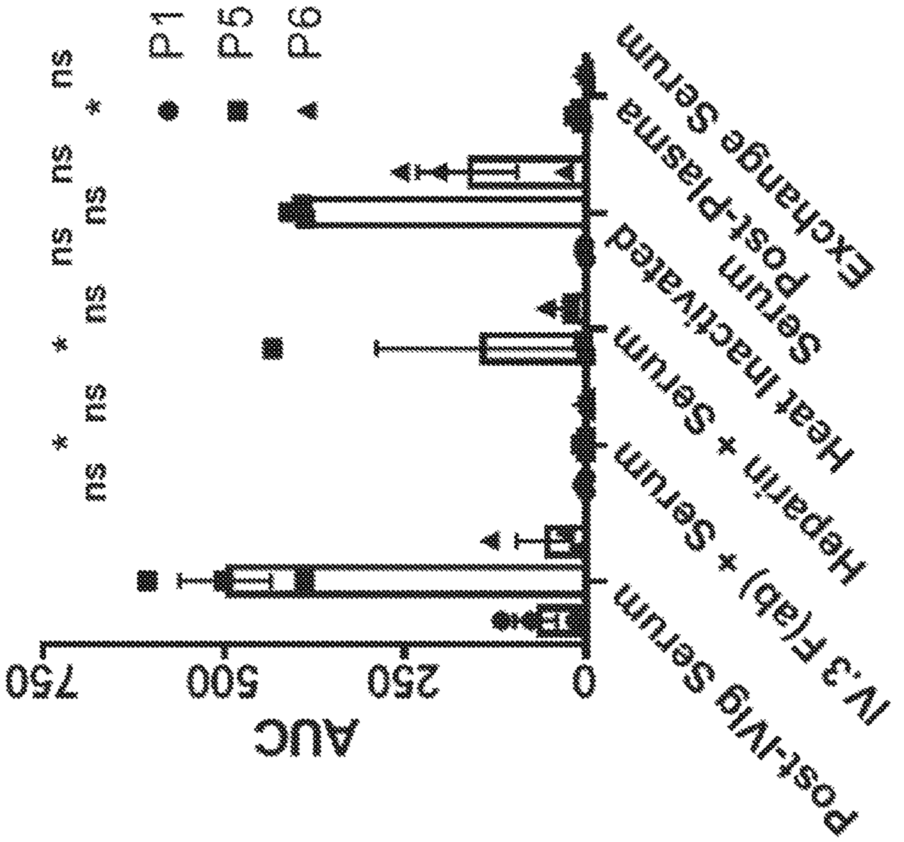

Serum was collected from healthy donors and patients with VITT. Patient 1 had serum collected after IVIg had been administered. Patients 2, 3 and 4 had serum collected both before and after IVIg administration. Patient 2 had received dexamethasone prior to their first serum collection. To investigate the effect on platelet activation, these sera were added to washed platelets and platelet aggregation was measured (FIGS. 1A-1C). Serum from patients with VITT triggered platelet aggregation to variable degrees depending on the platelet donor, which was abolished in post-IVIg treatment sera. Low-titer anti-PF4 antibodies have been shown to develop after vaccination in a small percentage of healthy individuals; however, they do not cause platelet activation. Aggregation was blocked after IVIg treatment, except in the 2 patients who did not clinically respond to IVIg and required plasma exchange (FIG. 1A). In these 2 patients, aggregation responses were blocked after plasma exchange. Eptifibatide treatment confirmed that responses were aggregation not agglutination. Three repeats were performed for each serum sample on platelets from healthy donors known to respond.

Addition of the integrin αIIbβ3 inhibitor eptifibatide (9 μM) inhibited the response to patient sera, confirming that this was aggregation rather than agglutination (data not shown).

C. Platelet Aggregation to Serum from Patients with VITT is Abolished by FCγRIIA Blockade and Heat Inactivation Platelet activation in HIT is caused by antibody mediated clustering of FcγRIIA. Greinacher et al., Autoimmune heparin-induced thrombocytopenia, J Thromb Haemost 15(11): 2099-114 (2017). To determine if a similar mechanism was involved in VITT we used an anti-FcγRIIA blocking IV.3 F(ab). Platelet activation by patient sera was abolished in the presence of IV.3 F(ab) demonstrating platelet activation in VITT is mediated via FcγRIIA (FIG. 1A).

The effects of PF4 and heparin in HIT in conjunction with patient sera were evaluated. Both PF4 and low concentrations of heparin have been shown to enhance platelet responses in HIT assays, whereas heparin at high concentrations inhibits any response. Rubino et al., A comparative study of platelet factor 4-enhanced platelet activation assays for the diagnosis of heparin-induced thrombocytopenia, H Thrombo Haemost 19(4):1096-102 (2021); Vayne et al., Beneficial effect of exogenous platelet factor 4 for detecting pathogenic heparin-induced thrombocytopenia antibodies, Br J Haematol 179(5):811-9 (2017); Padmanabhan et al., A novel PF4-dependent platelet activation assay identifies patients likely to have heparin-induced thrombocytopenia/thrombosis, Chest 150(3):506-15 (2016). No enhancement in the partial aggregation observed to patient 2 serum was observed in the presence of 10 μg/mL PF4 (data not shown). Low concentrations of heparin are known to enhance platelet responses in HIT assays, whereas high concentrations are inhibitory. In contrast, low (0.2 U/mL) concentrations of heparin prevented (5 of 7 patients) or delayed (2 of 7 patients) aggregation. High heparin concentration (100 U/mL) blocked aggregation (FIGS. 1B-1C).

Immune complexes that activate platelets via FcγRIIA have been reported in patients critically ill with COVID-19. In these patients, who had been exposed to heparin and displayed thrombocytopenia and thrombosis, HIT was ruled out, because of the lack of anti-PF4 antibodies and platelet activation independent of heparin. Platelet activation by these immune complexes was blocked by both low and high concentrations of heparin. We observed that heparin blocks platelet aggregation, which implies that the decision to withhold heparin use in patients with VITT perhaps should be revisited. Unfractionated heparin treatment has been reported in 1 patient with VITT without deleterious effect.

Anti-SARS-CoV-2 spike protein IgG antibodies from patients with severe COVID-19 have been shown to induce apoptosis and increase phosphatidylserine externalization in platelets mediated by FcγRIIA, although IgG aggregates or immune complexes could not be isolated from patient sera. It is possible that a similar mechanism is occurring in patients with VITT. Activation of FCγRIIA could give rise to phosphatidylserine exposure and procoagulant platelets, which may lead to the extensive thrombosis and thrombocytopenia observed in patients with VITT. To exclude platelet activation from other sources (such as thrombin and complement) in sera, heat inactivation (56° C., 45 minutes) of the three patient sera that caused activation was used. Warkentin et al., The platelet serotonin-release assay, Am J Hematol 90(6):564-72, doi:10.1002/ajh.24006 (2015). Heat inactivation of patient sera blocked aggregation in 3 of 7 patients (FIG. 1A), whereas minor effects on aggregation were observed with compstatin (a C3a inhibitor) and FUT-175 (a C3, C4, and C5 inhibitor; data not shown). These findings indicate that, although complement is not critical, it may reinforce platelet activation. Eculizumab (anti-C5 monoclonal antibody) treatment has been reported in 2 patients with VITT, in whom anticoagulation and IVIg or plasma exchange failed. Both patients rapidly improved. The involvement of complement, which mediates a broad range of thromboinflammatory reactions involving endothelium, monocytes, and neutrophils, as well as platelets, in VITT pathology should be considered. Normal serum complement levels in patients with VITT have been reported.

Figure 2B:
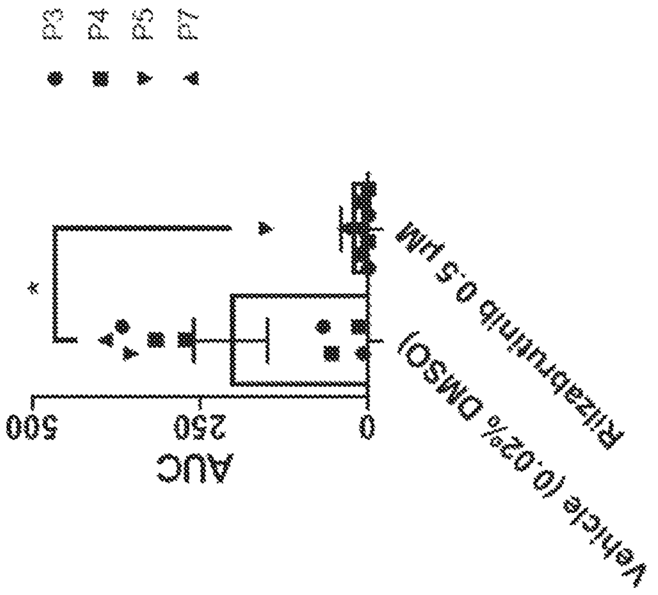
FIGS. 2A-B show the effect of Btk inhibition by rilzabrutinib, which blocks platelet aggregation induced by serum from patients with VITT. Washed platelets ($2\times10^8$/mL) were incubated with rilzabrutinib (0.5 μM) or vehicle (0.02% DMSO) for 10 minutes then stimulated with serum (1:15, v/v) from patients with VITT.
Figure 2A:
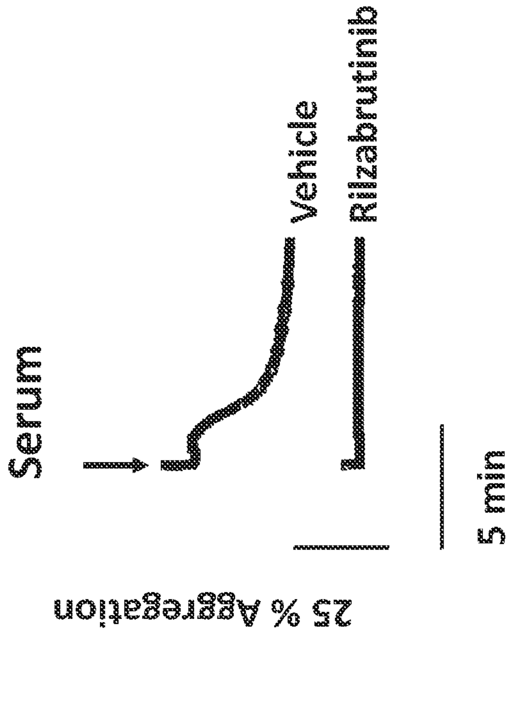

D. Inhibition of Bruton's Tyrosine Kinase (Btk) by Rilzabrutinib Blocks Platelet Aggregation Induced by VITT Patient Serum We tested if the Btk inhibitor rilzabrutinib (rilzabrutinib powder prepared in DMSO (final 0.02% DMSO) to achieve a concentration of 0.5 μM) could prevent platelet aggregation in patient sera. As shown in FIGS. 2A-2B, rilzabrutinib prevented platelet aggregation in patient sera (FIGS. 2A-B). Rilzabrutinib fully inhibited aggregation to 3 μg/mL collagen (results not shown).

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method for treating vaccine-induced thrombosis and thrombocytopenia syndrome (VITT) in a human subject in need thereof comprising administering to the human subject a therapeutically effective amount of at least one BTK inhibitor selected from:

Compound (I):

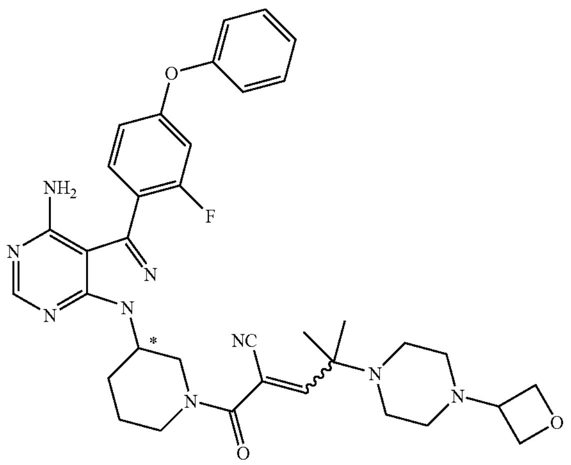

where *C is a stereochemical center,

Compound (II):

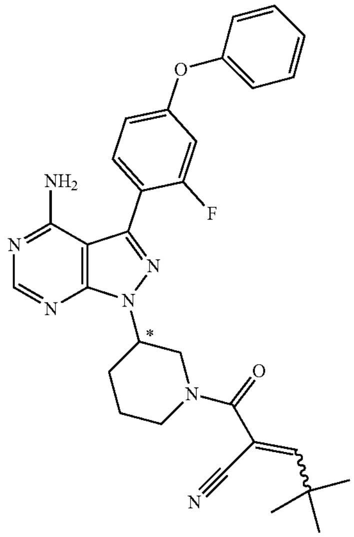 [SMILES: CC(C)(C)C=C(C#N)C(=O)N1CCCC(n2nc(-c3ccc(Oc4ccccc4)cc3F)c3c(N)ncnc32)C1]

where *C is a stereochemical center, and pharmaceutically acceptable salts thereof.

2. A method for increasing platelet count in a human subject with vaccine-induced thrombosis and thrombocytopenia syndrome (VITT) comprising administering to the human subject a therapeutically effective amount of at least one BTK inhibitor selected from:

Compound (I):

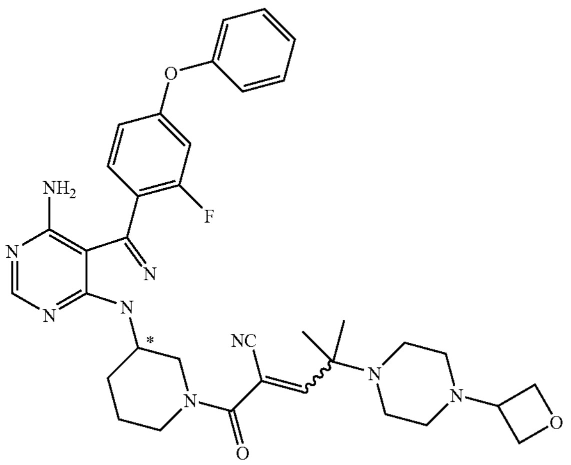

where *C is a stereochemical center,

Compound (II):

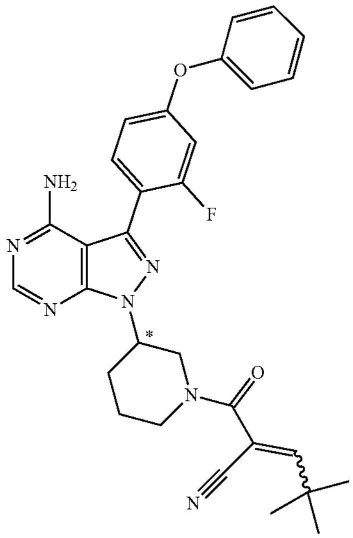 [SMILES: CC(C)(C)C=C(C#N)C(=O)N1CCCC(n2nc(-c3ccc(Oc4ccccc4)cc3F)c3c(N)ncnc32)C1]

where *C is a stereochemical center, and pharmaceutically acceptable salts thereof.

3. A method for reducing platelet aggregation in a human subject with vaccine-induced thrombosis and thrombocytopenia syndrome (VITT) comprising administering to the human subject a therapeutically effective amount of at least one BTK inhibitor selected from:

Compound (I):

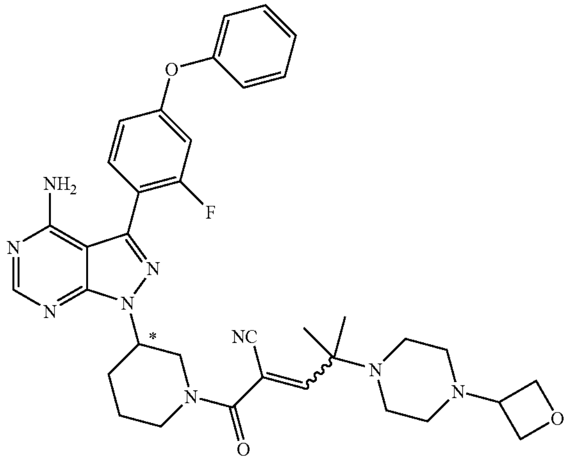

where *C is a stereochemical center,

Compound (II):

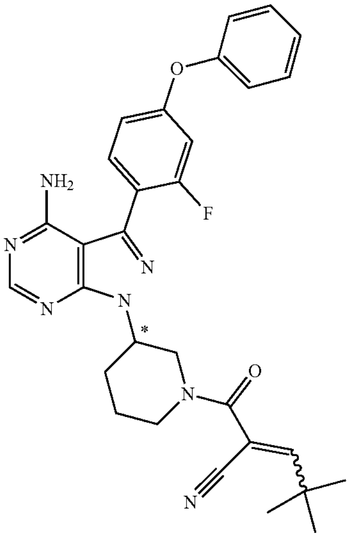 [SMILES: CC(C)(C)C=C(C#N)C(=O)N1CCCC(Nc2ncnc(N)c2C(=N)c2ccc(Oc3ccccc3)cc2F)C1]

where *C is a stereochemical center, and pharmaceutically acceptable salts thereof.

4. The method of claim 1, wherein, prior to administration, the human subject has at least one characteristic chosen from:

a. elevated D-dimer levels;

b. thrombosis; and c. anti-platelet factor 4 (PF4) antibodies.

5. The method of claim 1, wherein the vaccine-induced thrombosis and thrombocytopenia syndrome (VITT) is induced by administration of a vaccine.

6. The method of claim 1, wherein the vaccine-induced thrombosis and thrombocytopenia syndrome (VITT) is induced by administration of a vaccine delivered in an adenoviral vector.

7. The method of claim 6, wherein the adenoviral vector comprises a therapeutic agent, a prophylactic agent, or a therapeutic agent and a prophylactic agent.

8. The method of claim 7, wherein the therapeutic or prophylactic agent is a gene therapy.

9. The method of claim 5, wherein the vaccine is to prevent a coronavirus infection.

10. The method of claim 9, wherein the coronavirus infection is COVID-19.

11. The method of claim 5, wherein the vaccine is to prevent an infection selected from at least one of measles, mumps, rubella, varicella, herpes simplex virus 1, herpes simplex virus 2, varicella, rotavirus, influenza, yellow fever, smallpox, hepatitis B, human papilloma virus, pneumococcus, hepatitis A, anthrax, diphtheria, acellular pertussis, hemophilus influenzae, including type B, meningococcus C, meningitis, typhoid, rabies, Lyme disease, tetanus, and any combination thereof.

12. The method of claim 1, wherein Compound I is (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, a mixture of (R)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile and(S)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile; or an individual (E)- or (Z)-isomer of any of the above compounds; or a pharmaceutically acceptable salt of any of the above compounds.

13. The method of claim 12, wherein Compound I is the (E) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof; or wherein Compound I is the (Z) isomer of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof.

14. The method of claim 12, wherein Compound I is a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof.

15. The method of claim 1, wherein Compound II is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, a mixture of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile and(S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, or an individual (E)- or (Z)-isomer of any of the above compounds; or a pharmaceutically acceptable salt of any of the above compounds.

16. The method of claim 15, wherein Compound II is the (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof; or wherein Compound II is the (Z) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof.

17. The method of claim 15, wherein Compound II is a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile or a pharmaceutically acceptable salt thereof.

18. The method of claim 2, wherein Compound I is (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile, a mixture of (R)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile and(S)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile; or an individual (E)- or (Z)-isomer of any of the above compounds; or a pharmaceutically acceptable salt of any of the above compounds.

19. The method of claim 3, wherein Compound I is (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile, a mixture of (R)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile and(S)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile; or an individual (E)- or (Z)-isomer of any of the above compounds; or a pharmaceutically acceptable salt of any of the above compounds.

* * * * *